United States Patent
Zhou et al.

(10) Patent No.: US 9,498,674 B2
(45) Date of Patent: Nov. 22, 2016

(54) ELLIPTICAL PRONE EXERCISER

(71) Applicant: Lisha Zhou, Auckland (NZ)

(72) Inventors: Lisha Zhou, Auckland (NZ); Minghu Rao, Auckland (NZ)

(73) Assignee: Lisha Zhou, Auckland (NZ)

( * ) Notice: Subject to any disclaimer, the term of this patent is extended or adjusted under 35 U.S.C. 154(b) by 0 days.

(21) Appl. No.: 14/442,995

(22) PCT Filed: Mar. 12, 2014

(86) PCT No.: PCT/CN2014/073283
§ 371 (c)(1),
(2) Date: May 14, 2015

(87) PCT Pub. No.: WO2015/054986
PCT Pub. Date: Apr. 23, 2015

(65) Prior Publication Data
US 2015/0283425 A1   Oct. 8, 2015

(30) Foreign Application Priority Data

Oct. 16, 2013   (CN) .......................... 2013 1 0483930

(51) Int. Cl.
*A63B 69/10*   (2006.01)
*A63B 22/06*   (2006.01)
(Continued)

(52) U.S. Cl.
CPC .......... *A63B 22/0664* (2013.01); *A61B 5/222* (2013.01); *A63B 21/15* (2013.01); *A63B 22/001* (2013.01);
(Continued)

(58) Field of Classification Search
CPC ................... A63B 21/00058; A63B 21/00069; A63B 21/00076; A63B 21/00178;
(Continued)

(56) References Cited

U.S. PATENT DOCUMENTS 2,013,520 A * 9/1935 McDermott ........... A63B 69/10
482/56
3,791,646 A * 2/1974 Marchignoni ......... A63B 69/10
434/254
(Continued)

FOREIGN PATENT DOCUMENTS

AU   2010201876 A1   6/2010
CN   2226960 Y   5/1996
(Continued)

OTHER PUBLICATIONS

International Search Report dated Jul. 8, 2014 issued in counterpart International Application No. PCT/CN2014/073283.

*Primary Examiner* — Oren Ginsberg
*Assistant Examiner* — Gary D Urbiel Goldner
(74) *Attorney, Agent, or Firm* — Procopio, Cory, Hargreaves & Savitch, LLP

(57) ABSTRACT

An elliptical prone exerciser is disclosed, which comprises a frame (1), a front drive mechanism (3), a rear drive mechanism (4) and a damping wheel (2) arranged on the frame (1). The front drive mechanism (3) and the rear drive mechanism (4) are respectively arranged at a front end and a rear end of the frame (1). An output end of the front drive mechanism (3) and an output end of the rear drive mechanism (4) are respectively connected with the damping wheel (2). The front drive mechanism (3) is provided with a pair of movable hand support members (30), and the rear drive mechanism (4) is provided with a pair of movable knee support members (40). The pair of movable hand support members (30) and the pair of movable knee support members (40) move in an elliptical path. The elliptical prone exerciser is characterized by natural and coordinated motion, low impact and high safety.

21 Claims, 23 Drawing Sheets

(51) Int. Cl.
  *A63B 22/00* (2006.01)
  *A61B 5/22* (2006.01)
  *A63B 21/00* (2006.01)
  A63B 69/00 (2006.01)
  A63B 69/14 (2006.01)
  A63B 21/22 (2006.01)
  A63B 22/20 (2006.01)
  A61B 5/024 (2006.01)
  A61B 5/00 (2006.01)

(52) U.S. Cl.
  CPC ....... *A63B 22/0005* (2015.10); *A63B 22/0015* (2013.01); *A63B 22/0023* (2013.01); *A63B 22/0046* (2013.01); *A61B 5/024* (2013.01); *A61B 5/6895* (2013.01); *A63B 21/225* (2013.01); *A63B 22/203* (2013.01); *A63B 69/0057* (2013.01); *A63B 69/14* (2013.01); *A63B 2022/0033* (2013.01); *A63B 2022/067* (2013.01); *A63B 2022/0676* (2013.01); *A63B 2208/0219* (2013.01); *A63B 2208/0261* (2013.01); *A63B 2208/0295* (2013.01); *A63B 2230/06* (2013.01)

(58) Field of Classification Search
  CPC .................. A63B 21/00181; A63B 21/00185; A63B 21/00192; A63B 21/0056; A63B 21/0608; A63B 21/068; A63B 21/15; A63B 21/151; A63B 21/152; A63B 21/153; A63B 21/154; A63B 21/22; A63B 21/225; A63B 21/227; A63B 21/4033; A63B 21/4034; A63B 21/4035; A63B 21/4039; A63B 21/4045; A63B 21/4047; A63B 21/4049; A63B 22/0002; A63B 22/0005; A63B 22/001; A63B 22/0015; A63B 22/0017; A63B 22/0046; A63B 22/06; A63B 22/0664; A63B 22/20; A63B 22/201; A63B 22/203; A63B 2022/0043; A63B 2022/067; A63B 2022/0676; A63B 23/035; A63B 23/03516; A63B 23/03533; A63B 23/03541; A63B 23/03575; A63B 23/04; A63B 23/0405; A63B 23/0423; A63B 23/0476; A63B 23/0482; A63B 23/0494; A63B 23/12; A63B 23/1209; A63B 23/1218; A63B 23/1245; A63B 23/1263; A63B 23/1281; A63B 69/0048; A63B 69/0057; A63B 69/14; A63B 2208/0214; A63B 2208/0219; A63B 2208/0242; A63B 2208/0257; A63B 2208/0261; A63B 2208/0295; A63B 2230/06; A63B 2244/20
  See application file for complete search history.

(56) References Cited

U.S. PATENT DOCUMENTS

| | | | | |
|---|---|---|---|---|
| 4,674,740 | A * | 6/1987 | Iams | A63B 69/10 482/111 |
| 4,886,050 | A * | 12/1989 | Iams | A63B 23/0355 434/255 |
| 5,224,909 | A | 7/1993 | Hamilton | |
| 5,429,564 | A * | 7/1995 | Doane | A63B 69/10 434/254 |
| 5,540,591 | A * | 7/1996 | Doane | A63B 69/10 434/254 |
| 5,685,804 | A | 11/1997 | Whan-Tong et al. | |
| 7,998,043 | B2 * | 8/2011 | Zhou | A63B 21/154 482/139 |
| 2002/0132706 | A1 * | 9/2002 | Sleamaker | A63B 21/068 482/51 |
| 2003/0092533 | A1 * | 5/2003 | Hippensteel | A63B 23/03575 482/56 |
| 2008/0051258 | A1 * | 2/2008 | Schmehl | A63B 22/0015 482/52 |
| 2009/0105050 | A1 | 4/2009 | Mayo | |
| 2010/0048367 | A1 | 2/2010 | Liang et al. | |
| 2010/0248919 | A1 * | 9/2010 | Zhou | A63B 21/154 482/139 |
| 2012/0244998 | A1 * | 9/2012 | Rao | A63B 71/0054 482/70 |
| 2014/0011645 | A1 * | 1/2014 | Johnson | A63B 21/4033 482/121 |
| 2014/0371036 | A1 * | 12/2014 | Ellis | A63B 23/0227 482/66 |
| 2015/0065311 | A1 * | 3/2015 | Rao | A63B 71/0054 482/70 |
| 2015/0141210 | A1 * | 5/2015 | Hall | A63B 69/10 482/56 |
| 2015/0151158 | A1 * | 6/2015 | Ellis | A63B 23/0205 482/142 |
| 2015/0328520 | A1 * | 11/2015 | Barnes | A63B 21/00185 482/56 |
| 2016/0059061 | A1 * | 3/2016 | Lagree | A63B 21/00065 482/92 |

FOREIGN PATENT DOCUMENTS

| | | |
|---|---|---|
| CN | 201500415 U | 6/2010 |
| CN | 203494104 U | 3/2014 |
| KR | 20020025307 A | 4/2002 |

* cited by examiner

ELLIPTICAL PRONE EXERCISER

CROSS REFERENCING TO RELATED APPLICATIONS

This application is a 371 National Stage of International application number PCT/CN2014/073283 filed on 12 Mar. 2014, which claims the benefit of Chinese application number 201310483930.2 filed on 16 Oct. 2013. The contents of each of the above applications are incorporated by reference herein in their entirety.

FIELD

The invention relates to a horizontal exerciser, in particular to an elliptical prone exerciser.

BACKGROUND OF THE INVENTION

To all motions by human in an upright position, like standing, sitting, running or making upright motions on an exerciser, the gravity has negative effects on the human body. These negative effects from the gravity include lumbar vertebra and cervical vertebra diseases, knee joint injury, visceroptosis, cardiovascular and cerebrovascular diseases, etc. Corresponding to the upright motion, the movement with most of human body in a horizontal plane is called horizontal motion. For example, swimming is a typical horizontal motion widely known. As the negative effects of gravity is greatly reduced when human body is in a horizontal plane, the horizontal motion is considered as a more scientific and reasonable motion. Therefore, various horizontal-motion exercising devices are developed continuously.

Inventions, such as "Mid-Body Exercise Device" disclosed in patent documents with publication number of U.S. Pat. No. 5,224,909A, "Exercise Machine for Back Rehabilitation" disclosed in patent documents with publication number of US20090105050A1, and "Prone Exerciser" disclosed in patent documents with publication number of US20100048367A1, are capable of ensuring users to do motions that mimic crawling and swimming in a horizontal plane. These motions are linear reciprocating motion, but the real crawling or swimming motion is not linear (when crawling, human's hand and knee move in an elliptical path). What is more, impact which easily occurs at two ends of the linear reciprocating motion results in an unsmooth and uncoordinated motion which may cause injury to human body.

SUMMARY OF THE INVENTION

In order to overcome the defects in the prior art, the invention provides an elliptical prone exerciser having the advantages of natural and coordinated motion, low impact and high safety. The invention adopts the following technical proposal for solving the technical problems:

An elliptical prone exerciser comprises a frame, a front drive mechanism, a rear drive mechanism and a damping wheel arranged on the frame. The front drive mechanism and the rear drive mechanism are respectively arranged at the front end and rear end of the frame, the output ends of both the front drive mechanism and the rear drive mechanism are connected with the damping wheel, the front drive mechanism is provided with a pair of movable hand support members, the rear drive mechanism is provided with a pair of movable knee support members, and the movable hand support members and the movable knee support members move in an elliptical path.

The front drive mechanism comprises a front-drive synchronous transmission pair as well as a pair of front-drive swinging rods, a pair of front-drive connecting rods and a pair of front-drive cranks which are respectively arranged at both sides of the front-drive synchronous transmission pair; one end of the front-drive swinging rod is articulated with the middle of the frame while the other end articulated with one end of the front-drive connecting rod; the other end of the front-drive connecting rod is articulated with the front-drive cranks; the front-drive cranks are connected with the front-drive synchronous transmission pair and inputted with a rotating torque; the output end of the front-drive synchronous transmission pair is connected with the damping wheel; and the movable hand support members are arranged in the middle of the front-drive connecting rod.

The movable hand support members comprise a first gripping part and a second gripping part respectively arranged above and at the side of the front-drive connecting rod.

The rear drive mechanism comprises a rear-drive synchronous transmission pair as well as a pair of rear-drive swinging rods, a pair of rear-drive connecting rods and a pair of rear-drive cranks which are respectively arranged at both sides of the rear-drive synchronous transmission pair; one end of the rear-drive swinging rod is articulated with the middle of the frame while the other end articulated with one end of the rear-drive connecting rod; the other end of the rear-drive connecting rod is articulated with the rear-drive cranks; the rear-drive cranks are connected with the rear-drive synchronous transmission pair and inputted with a rotating torque; the output end of the rear-drive synchronous transmission pair is connected with the damping wheel; and the movable knee support members are arranged in the middle of the rear-drive connecting rod.

The movable knee support members are arranged above or hanged at one side of the rear-drive connecting rod.

Pedals are arranged at the joint where the rear-drive connecting rod is articulated with the rear-drive cranks.

A U-shaped connector is arranged at the joint where the rear-drive connecting rod is articulated with the rear-drive cranks, and two ends of the U-shaped connector are respectively connected with the two ends of the revolving shaft of the pedals.

The rear drive mechanism comprises a rear-drive synchronous transmission pair as well as a pair of rear-drive guide rails, a pair of rear-drive sliding wheels, a pair of rear-drive connecting rods and a pair of rear-drive cranks which are respectively arranged at both sides of the rear-drive synchronous transmission pair; the rear-drive guide rails is connected with the rear end of the frame; one end of the rear-drive connecting rod is slidingly arranged on the rear-drive guide rails through the rear-drive sliding wheels, while the other end is articulated with the rear-drive cranks; the rear-drive cranks are connected with the rear-drive synchronous transmission pair and inputted with a rotating torque; the output end of the rear-drive synchronous transmission pair is connected with the damping wheel; and the movable knee support members are arranged in the middle of the rear-drive connecting rod.

Pedals are arranged on the rear-drive connecting rod in a position near the rear-drive sliding wheels.

The front end of the rear-drive guide rail is articulated with the rear end of the frame and a positioning device used for the folding and fixing of the rear-drive guide rail against the frame is arranged on the rear-drive guide rail.

An adjusting device used for adjusting the incline angle is arranged on the frame, which comprises an adjusting bracket and an extension pushrod; one end of the adjusting bracket is articulated with the front part of the frame while the other end is provided with a glide wheel; and one end of the extension pushrod is articulated with the adjusting bracket while the other end is articulated with the frame.

The front drive mechanism or the rear drive mechanism is provided with a motor drive device used for providing driving force.

The frame is provided with a pair of safe handrails which are separately arranged at two sides of the front-drive mechanism.

The front part of the frame is provided with an elbow supporting pad, a heart-rate monitoring handle and a data display; the data display is fixed at the front end of the frame; and the heart-rate monitoring handle is arranged between the elbow supporting pad and the data display.

A chest and abdomen pad is arranged in the middle of the frame.

Both the pair of movable hand support members and the pair of the movable knee support members are arranged symmetrically.

The damping wheel is an inertial wheel or a magnetic-control wheel.

A plurality of front-drive crank adjusting holes used for length adjustment are cut on the front-drive cranks and the front-drive cranks are connected with the front-drive synchronous transmission pair by front-drive crank adjusting plug pins which pass through the front-drive crank adjusting holes.

A plurality of rear-drive crank adjusting holes used for length adjustment are cut on the rear-drive cranks and the rear-drive cranks are connected with the rear-drive synchronous transmission pair by rear-drive crank adjusting plug pins which pass through the rear-drive crank adjusting holes.

Compared with the prior art, the invention has the advantages that:

In the elliptical prone exerciser of the invention, the movable hand support members and the movable knee support members creates an elliptical, natural and coordinated motion that mimics a real prone crawling motion; compared with the lineal reciprocating motion, the elliptical motion significantly reduces motion impact, improves fitness effect, and lowers the injury risk of user's joints and muscles.

Figure 1:
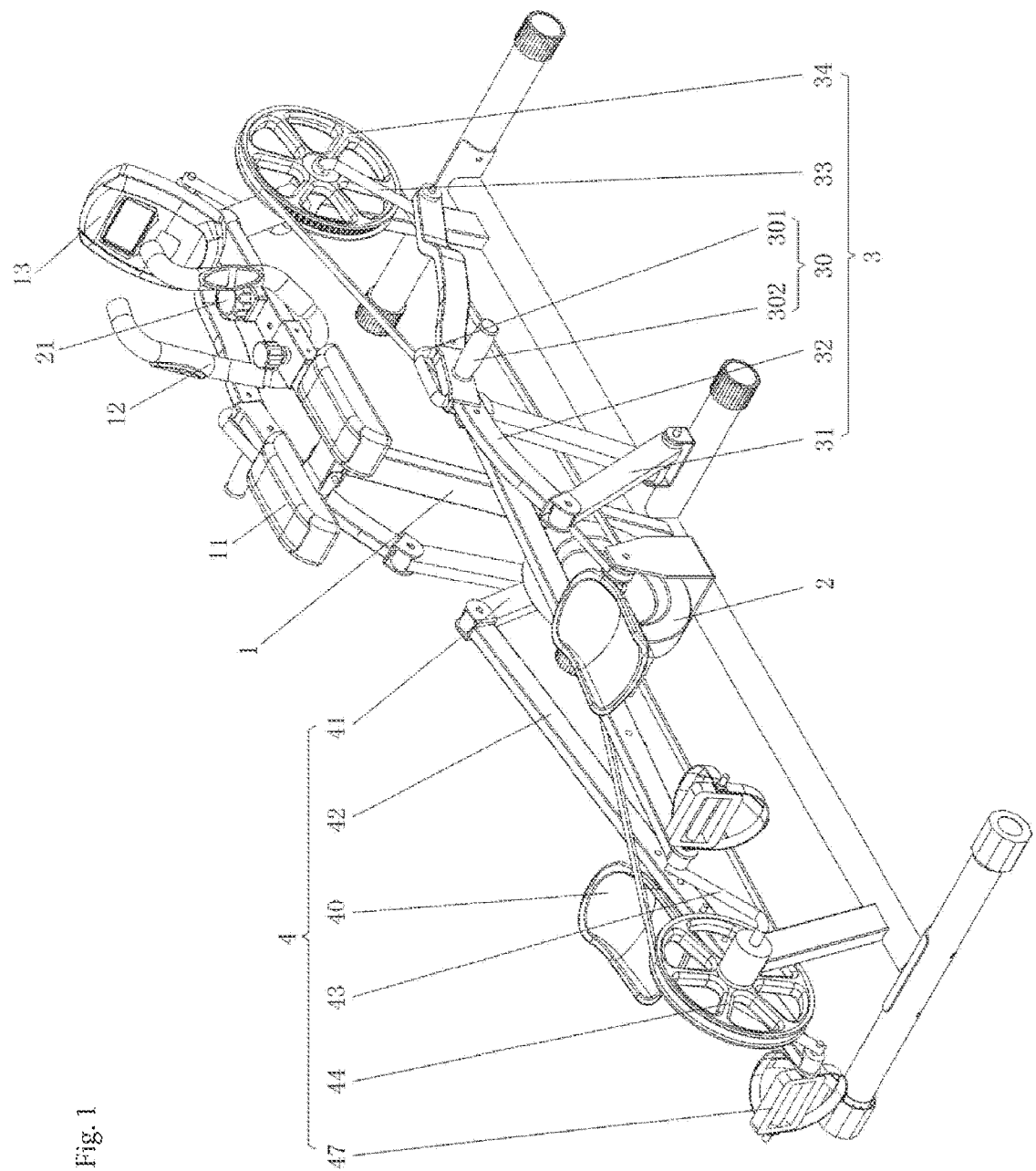
FIG. 1 is a first perspective view showing the three-dimensional structure of Embodiment 1.
Figure 2:
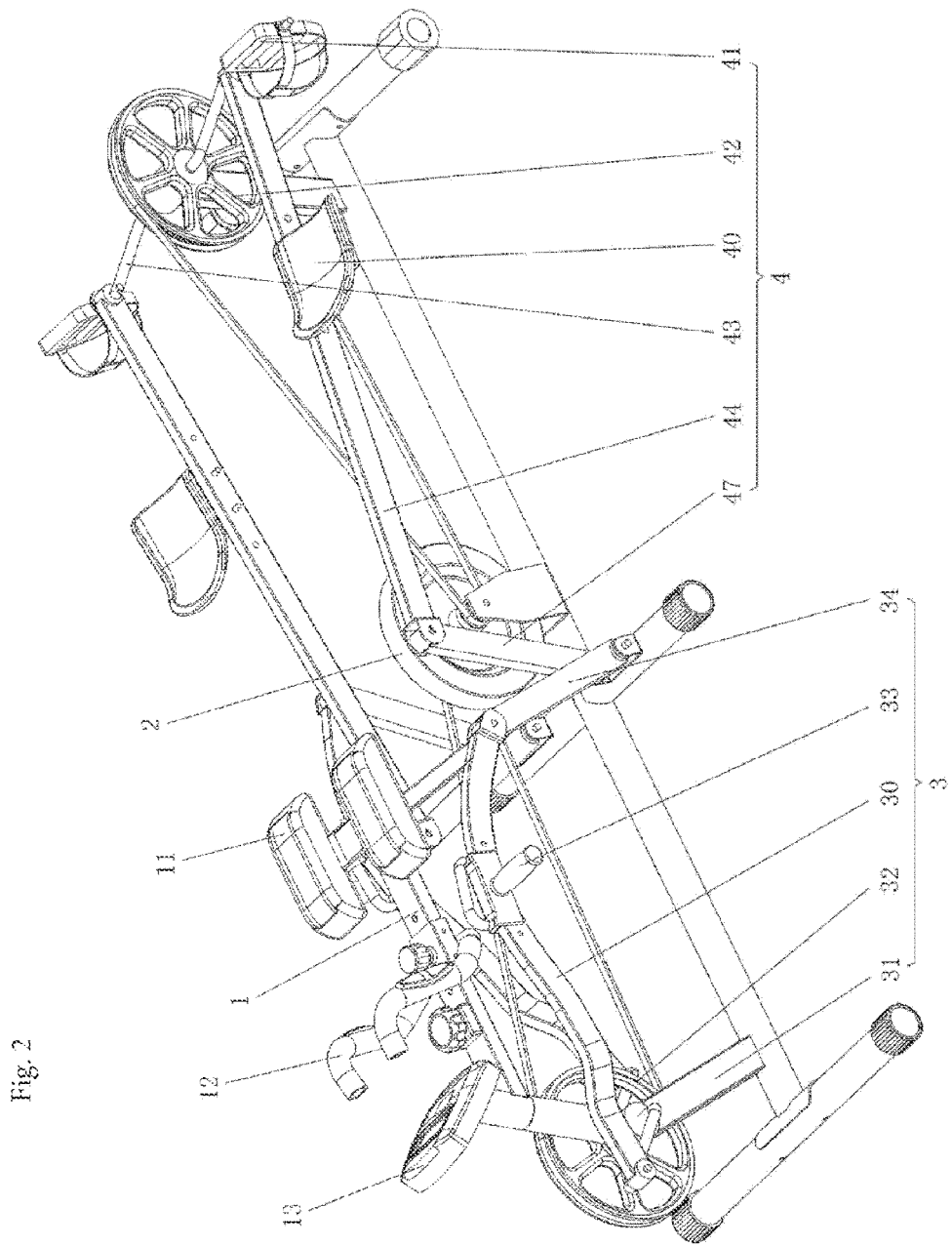
FIG. 2 is a second perspective view showing the three-dimensional structure of Embodiment 1.
Figure 3:
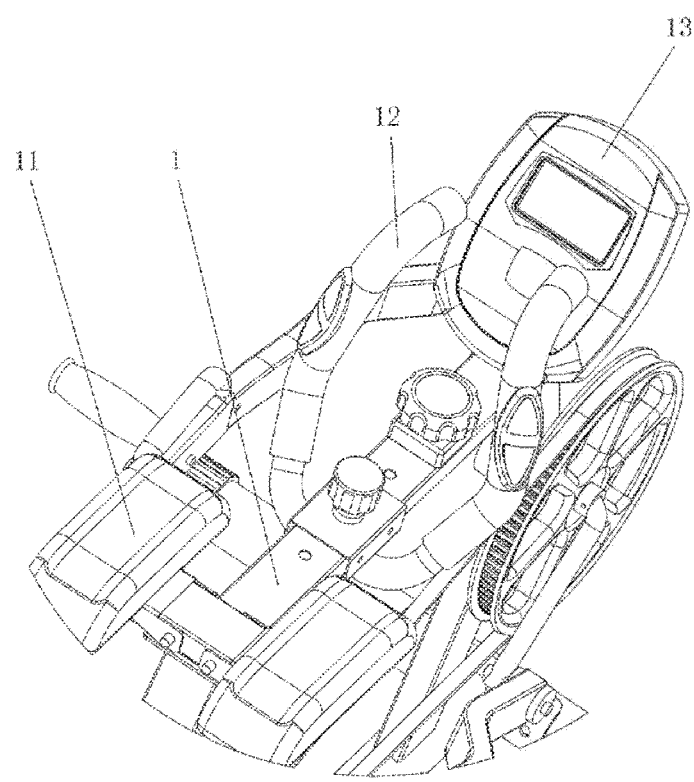
FIG. 3 is a view showing the three-dimensional structure of the elbow supporting pad, heart-rate monitoring handle and data display of Embodiment 1.
Figure 4:
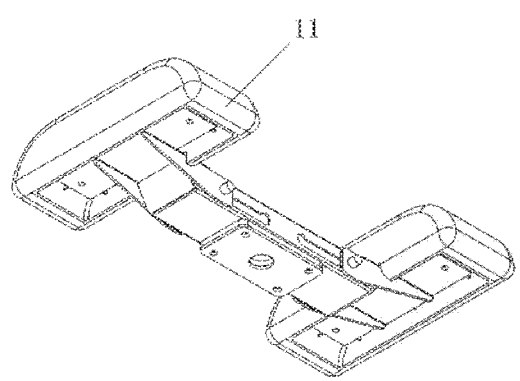
FIG. 4 is a view showing the adjustment of the elbow supporting pad of Embodiment 1.

Reference numerals in the figures:
1. Frame; 11. Elbow supporting pad; 12. Heart-rate monitoring handle; 13. Data display; 14. Chest and abdomen pad; 2. Damping wheel; 21. Damper regulator; 3. Front drive mechanism; 30. Movable hand supporting member; 301. First gripping part; 302. Second gripping part; 31. Front-drive swinging rod; 32. Front-drive connecting rod; 33. Front-drive cranks; 331. Front-drive crank adjusting holes; 332 Front-drive crank adjusting plug pins; 34. Front-drive synchronous transmission pair; 4. Rear drive mechanism; 40. Movablelcnee support members; 41. Rear-drive swinging rod; 42. Rear-drive connecting rod; 421. U-shaped connector; 43. Rear-drive cranks; 431. Rear-drive crank adjusting holes; 432. Rear-drive crank adjusting plug pins; 44. Rear-drive synchronous transmission pair; 45. Rear-drive guide rail; 46. Rear-drive sliding wheel; 47. Pedals; 48. Positioning device; 5. Adjusting device; 51. Adjusting bracket; 52. Extension pushrod; 53. Glide wheel; 6. Motor drive device; 7. Safe handrails.

DETAILED DESCRIPTION OF THE PREFERRED EMBODIMENTS

Embodiment 1: one embodiment of an elliptical prone exerciser is shown in FIGS. 1 to 4. The elliptical prone exerciser comprises a frame 1, a front drive mechanism 3, a rear drive mechanism 4 and a damping wheel 2 arranged on the frame 1. The front drive mechanism 3 and the rear drive mechanism 4 are respectively arranged at the front end and rear end of the frame 1, The output ends of both the front drive mechanism 3 and the rear drive mechanism 4 are connected with the damping wheel 2. The front drive mechanism 3 is provided with a pair of movable hand support members 30, and the rear drive mechanism 4 is provided with a pair of movable knee support members 40. The movable hand support members 30 and the movable knee support members 40 move in an elliptical path, thus creating an elliptical, natural and coordinated motion that mimics a real prone crawling motion. Compared with the linear reciprocating motion, the elliptical motion significantly reduces motion impact, improves fitness effect and lowers the injury risk of user's joints and muscles.

In this embodiment, the front drive mechanism 3 comprises a front-drive synchronous transmission pair 34 as well as a pair of front-drive swinging rods 31, a pair of front-drive connecting rods 32 and a pair of front-drive cranks 33 which are respectively arranged at both sides of the front-drive synchronous transmission pair 34. One end of the front-drive swinging rod 31 is articulated with the middle of the frame I while the other end articulated with one end of the front-drive connecting rod 32. The other end of the front-drive connecting rod 32 is articulated with the front-drive cranks 33. The front-drive cranks 33 are connected with the front-drive synchronous transmission pair 34 and inputted with a rotating torque. The output end of the front-drive synchronous transmission pair 34 is connected with the damping wheel 2. The movable hand support members 30 are arranged in the middle of the front-drive connecting rod 32. The front-drive swinging rods 31, the front-drive connecting rods 32 and the front-drive cranks 33 form a crank swinging-rod mechanism. The movable hand support members 30 moves with the front-drive connecting rod 32 in an elliptical path. Comprising a first gripping part 301 and a second gripping part 302 respectively arranged above and at the side of the front-drive connecting rod 32, the movable hand support members 30 provides users with easy gripping change and fatigue relief In this embodiment, a rear drive mechanism 4 comprises a rear-drive synchronous transmission pair 44 as well as a pair of rear-drive swinging rods 41, a pair of rear-drive connecting rods 42 and a pair of rear-drive cranks 43 which are respectively arranged at both sides of the rear-drive synchronous transmission pair 44; one end of the rear-drive swinging rod 41 is articulated with the middle of the frame 1 while the other end articulated with one end of the rear-drive connecting rod 42; the other end of the rear-drive connecting rod 42 is articulated with the rear-drive cranks 43; the rear-drive cranks 43 are connected with the rear-drive synchronous transmission pair 44 and inputted with a rotating torque; the output end of the rear-drive synchronous transmission pair 44 is connected with the damping wheel 2; and the movable knee support members 40 are arranged in the middle of the rear-drive connecting rod 42. The rear-drive swinging rods 41, the rear-drive connecting rods 42 and the rear-drive cranks 43 form a crank swinging-rod mechanism. The movable knee support members 40 moves with the rear-drive connecting rod 42 in an elliptical path and are arranged above or hanged at one side of the rear-drive connecting rod 42. In this embodiment, the movable knee support members 40 are arranged on one side of the rear-drive connecting bar 42 and made of elastic and soft pad. In this embodiment, pedals 47 are arranged at the joint where the rear-drive connecting rod 42 is articulated with the rear-drive cranks 43, and hanged at one side of the rear-drive connecting rod 42. Both the front-drive synchronous transmission pair 34 and the rear-drive synchronous transmission air 44 are synchronous belt-wheel transmission pair. The linkage between the front-drive synchronous transmission pair 34 and the rear-drive synchronous transmission pair 44 can ensure the upper and lower extremity movements are consistent and coordinated.

In this embodiment, the front part of the frame 1 is provided with an elbow supporting pad 11, a heart-rate monitoring handle 12 and a data display 13; the data display 13 is fixed at the front end of the frame 1; and the heart-rate monitoring handle 12 is arranged between the elbow supporting pad 11 and the data display 13. When heart rate monitoring is needed, the user can put elbow on the elbow supporting pad 11 and grip the heart-rate monitoring handle 12 with two hands, and the data display 13 shows the reading of the heart rate. The working principle of the heart-rate monitoring handle 12, which is the same as the heart rate monitor of a treadmill, is not elaborated herein. In addition, the position of the elbow supporting pad 11 and the heart-rate monitoring handle 12 can be adjusted forward or backward on the frame 1. The width of the elbow supporting pad 11 can be adjusted to adapt to the needs of different users and to avoid the interference to the movable hand supporting members 30 which are in motion.

In this embodiment, the frame 1 is provided with a damper regulator 21 to control the damping of the damping wheel 2. The damping wheel 2 may be an inertial wheel or a magnetic-control wheel, and this embodiment chooses a magnetic-control wheel as the damping wheel. The damping wheel 2 ensures a smoother and more coordinated motion and is capable of adjusting motion strength.

Figure 5:
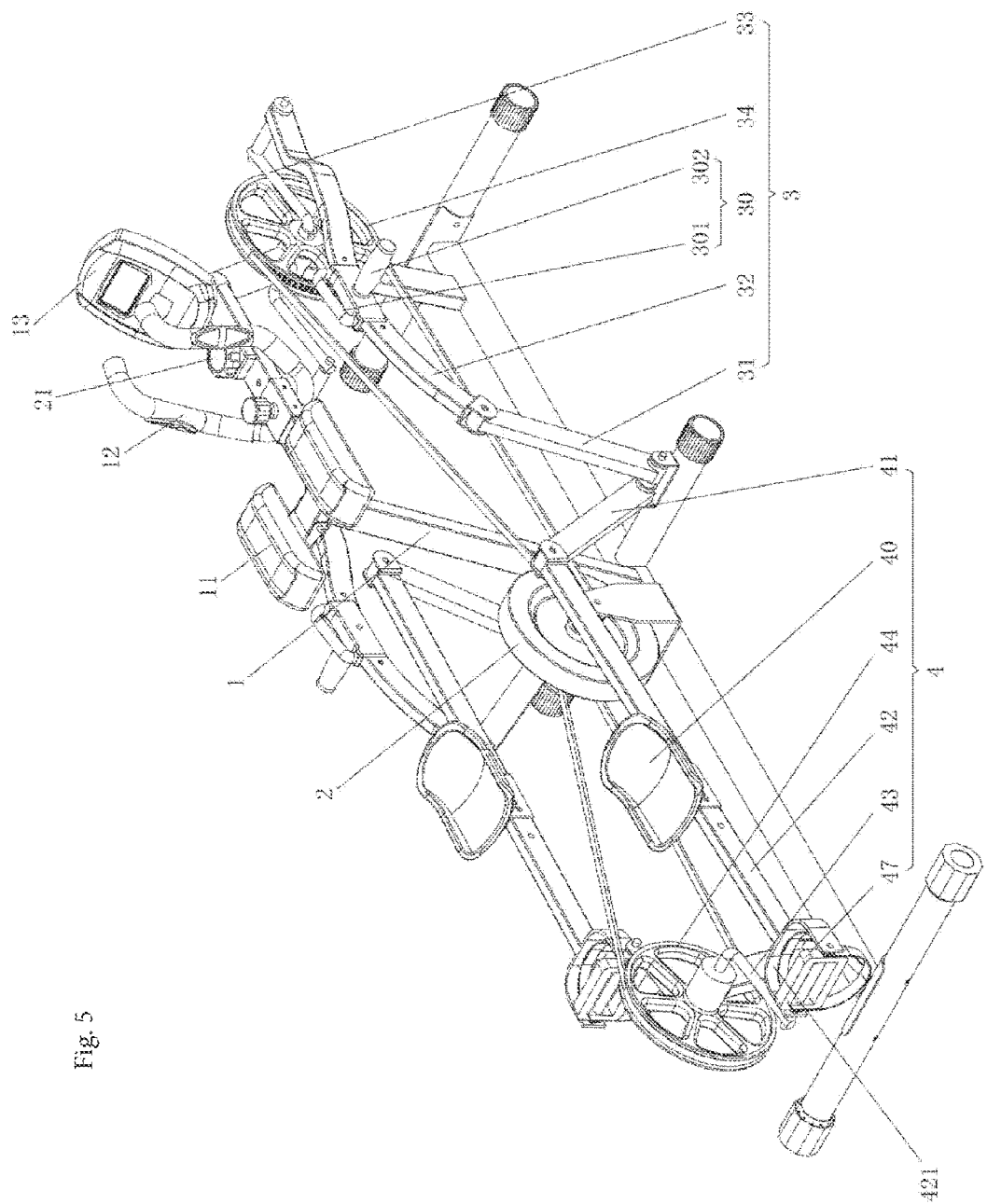
FIG. 5 is a first perspective view showing the three-dimensional structure of Embodiment 2.
Figure 6:
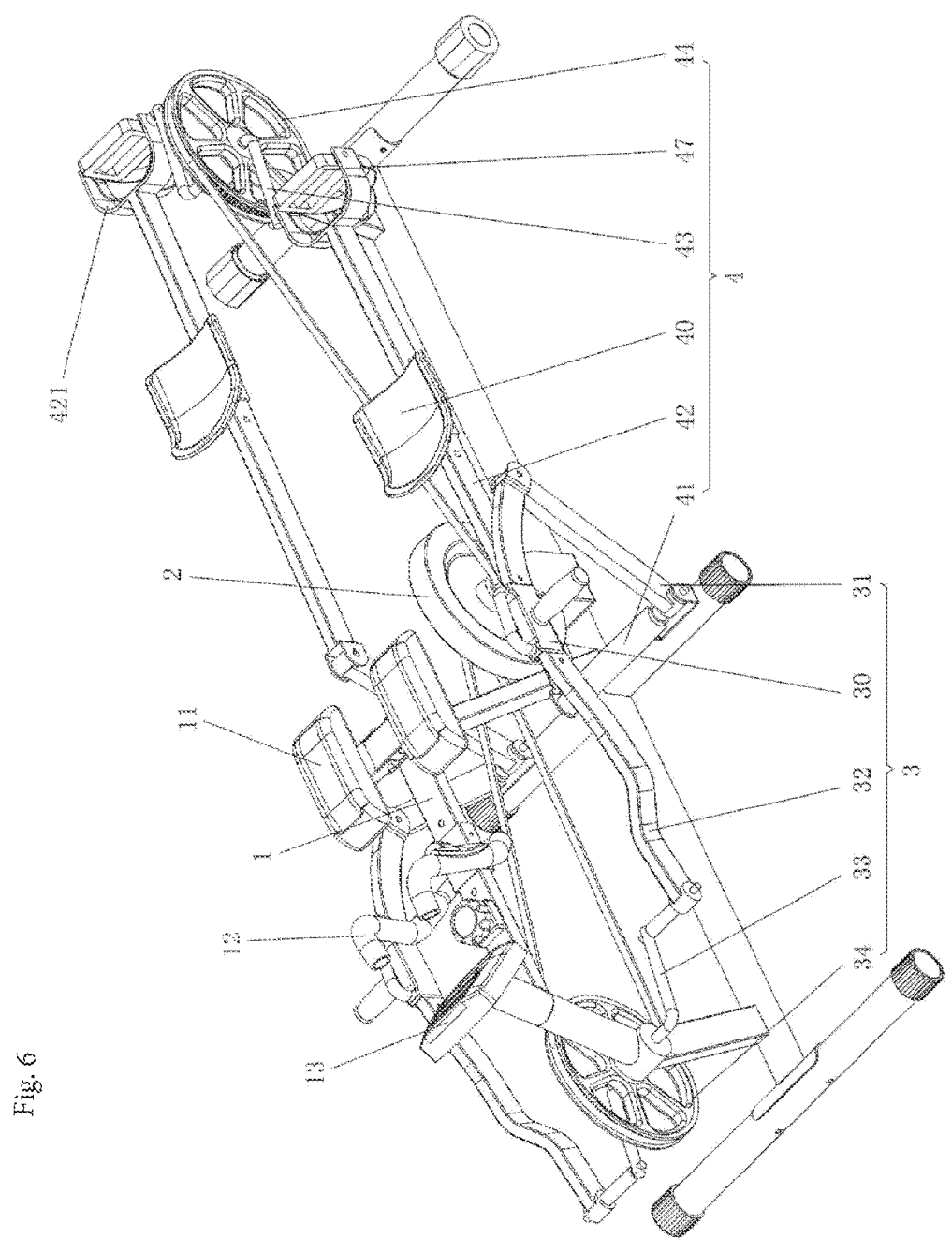
FIG. 6 is a second perspective view showing the three-dimensional structure of Embodiment 2.
Figure 7:
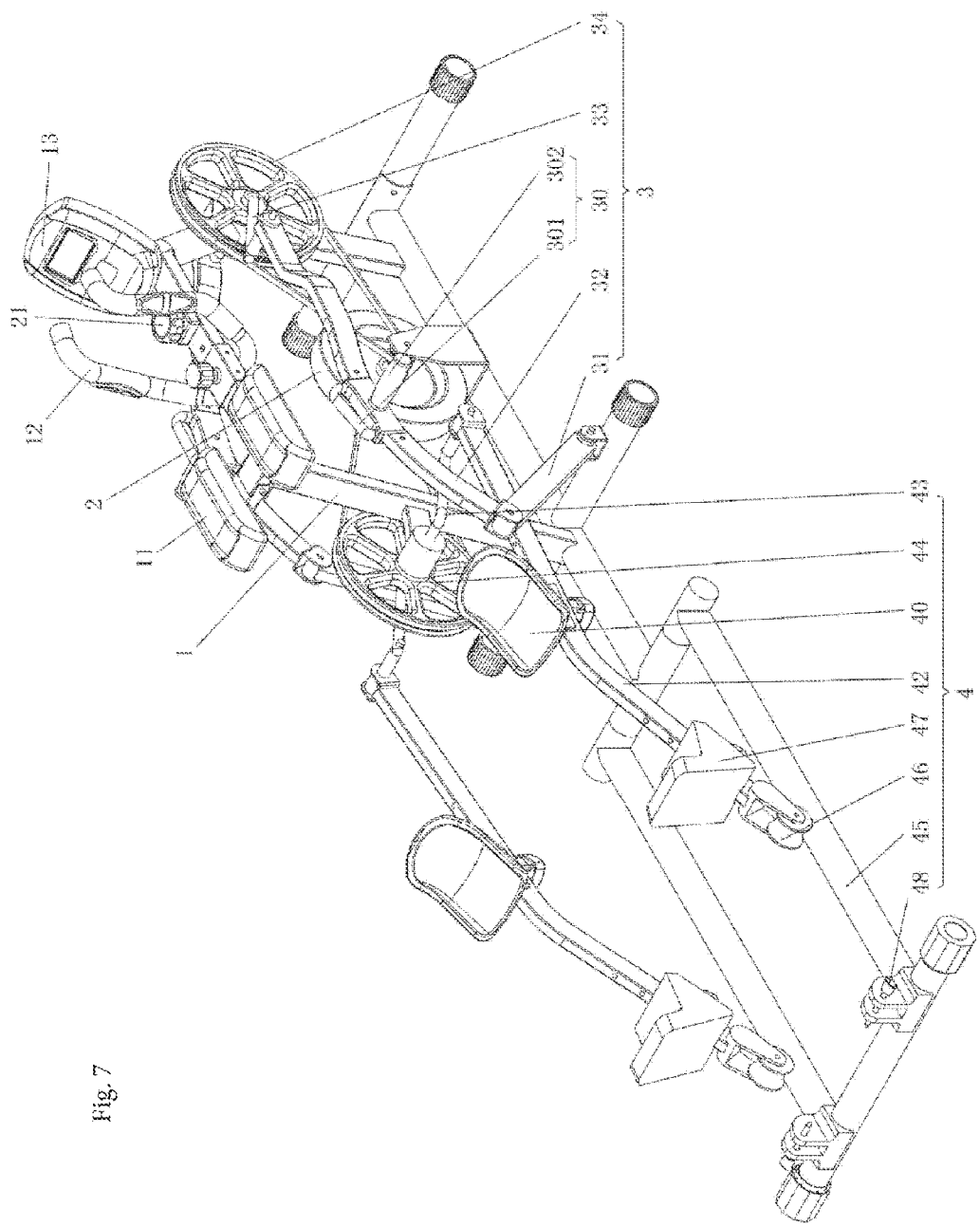
FIG. 7 is a first perspective view showing the three-dimensional structure of Embodiment 3.
Figure 8:
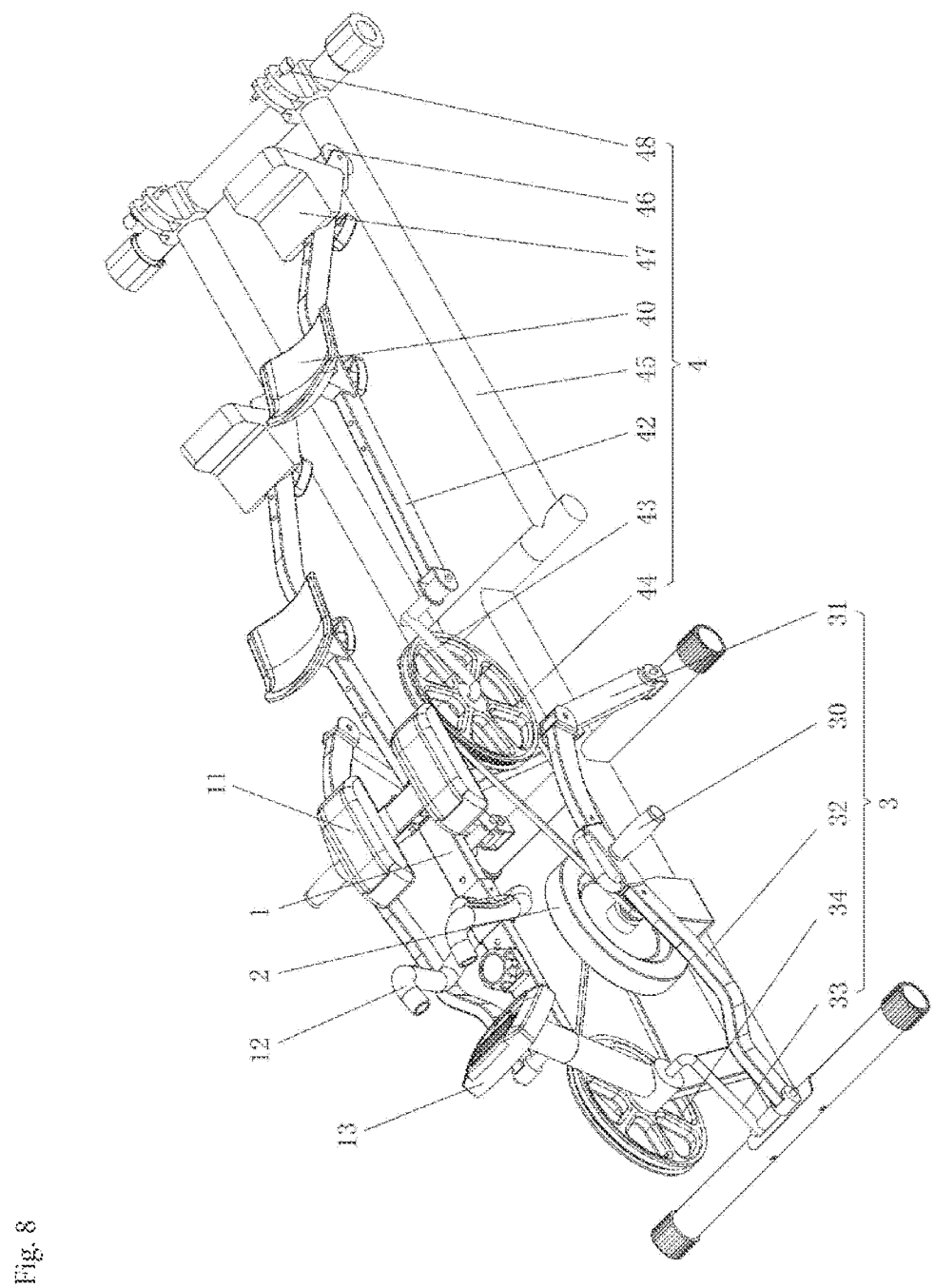
FIG. 8 is a second perspective view showing the three-dimensional structure of Embodiment 3.

Embodiment 2: the second embodiment of an elliptical prone exerciser is shown in FIGS. 5 and 6. This embodiment is basically the same as Embodiment 1, with the difference in that: the movable knee supporting member 40 is arranged above the rear-drive connecting rod 42; a U-shaped connector 421 is arranged at the joint where the rear-drive connecting rod 42 is articulated with the rear-drive cranks 43, and two ends of the U-shaped connector are connected with the two ends of the revolving shaft of the pedals 47. The structure of Embodiment 2 is more stable and bearable.

Embodiment 3: the third embodiment of an elliptical prone exerciser is shown in FIG. 7-10. This embodiment is basically the same as Embodiment 1, with the difference in that: the rear drive mechanism 4 comprises a rear-drive synchronous transmission pair 44 as well as a pair of rear-drive guide rails 45, a pair of rear-drive sliding wheels 46, a pair of rear-drive connecting rods 42 and a pair of rear-drive cranks 43 which are respectively arranged at both sides of the rear-drive synchronous transmission pair 44; the rear-drive guide rails 45 is connected with the rear end of the frame 1; one end of the rear-drive connecting rod 42 is slidingly arranged on the rear-drive guide rails 45 through the rear-drive sliding wheels 46 while the other end is articulated with the rear-drive cranks 43; the rear-drive cranks 43 are connected with the rear-drive synchronous transmission pair 44 and inputted with a rotating torque; the output end of the rear-drive synchronous transmission pair 44 is connected with the damping wheel 2; and the movable knee support members 40 are arranged in the middle of the rear-drive connecting rod 42. The rear-drive guide rails 45, the rear-drive sliding wheels 46, the rear-drive connecting rods 42 and the rear-drive cranks 43 forms a crank sliding-block mechanism. The movable knee supporting member 40 moves with the rear-drive connecting rod 42 in an elliptical path. Pedals 47 are arranged on the rear-drive connecting rod 42 in a position near the rear-drive sliding wheels 46. The pedals 47 of this embodiment are in linear reciprocating motion.

Figure 9:
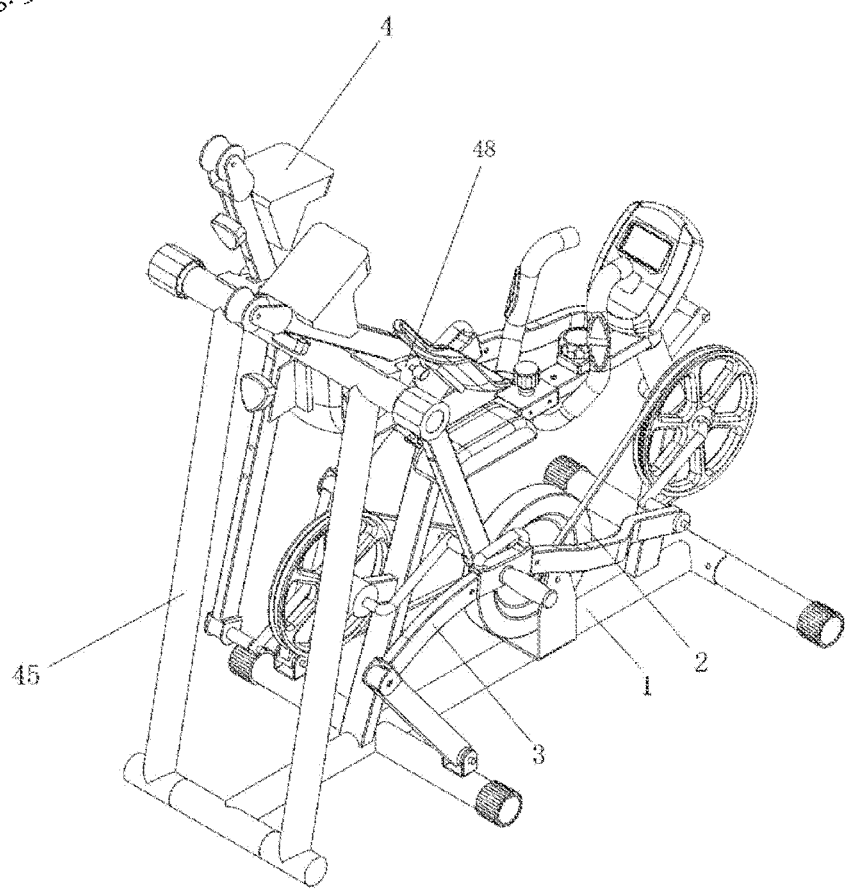
FIG. 9 is a first perspective view showing the three-dimensional structure of the folded form of Embodiment 3.
Figure 10:
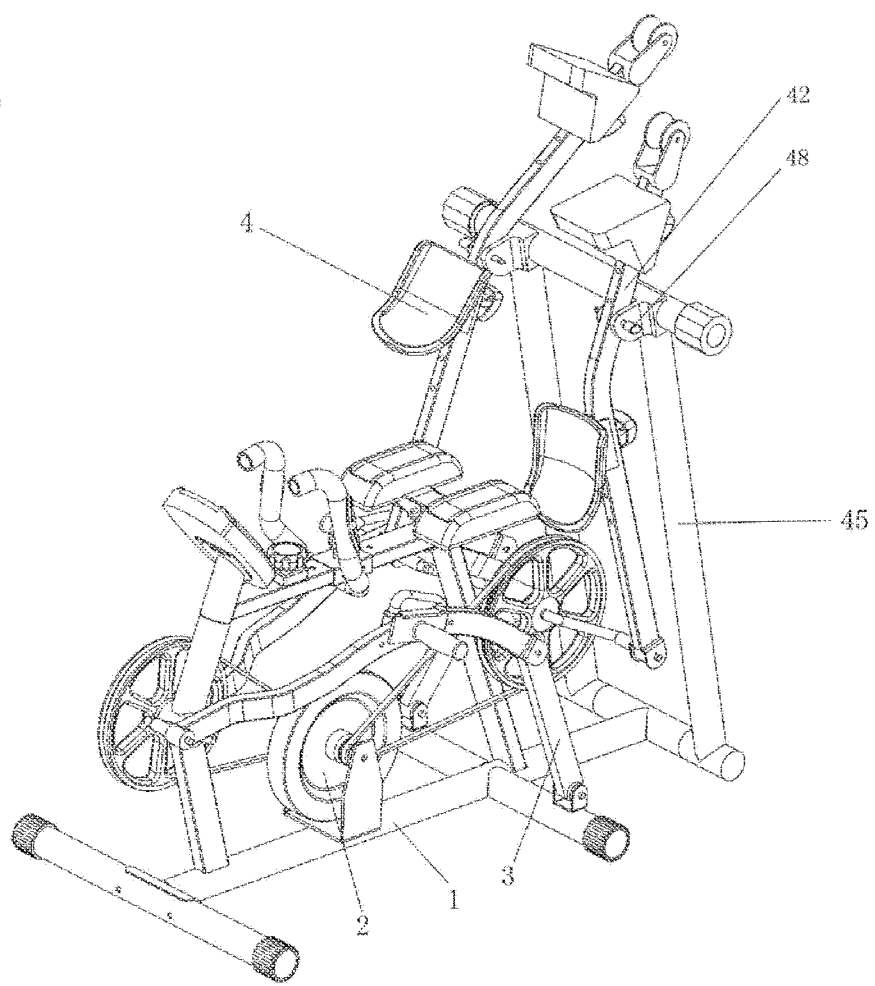
FIG. 10 is a second perspective view showing the three-dimensional structure of the folded form of Embodiment 3.

In this embodiment, the front end of the rear-drive guide rail 45 is articulated with the rear end of the frame 1 and a positioning device 48 used for the folding and fixing of the rear-drive guide rail 45 against the frame 1 is arranged on the rear-drive guide rail 45. When put away or transported, the rear-drive guide rail 45 can be folded against the frame 1 (as shown in FIG. 9 and FIG. 10) to save space, and meanwhile fixed with the rear-drive connecting rod 42 with the positioning device 48, thus preventing the rear-drive guide rail 45 from falling down and ensuring a reliable and stable connection. When in use, the rear-drive guide rail 45 is unfolded to parallel to the frame 1. The positioning device 48 of this embodiment is a bolt, and a buckle or clip which ensures reliable connection and convenient operation is also selectable for other embodiments.

Figure 11:
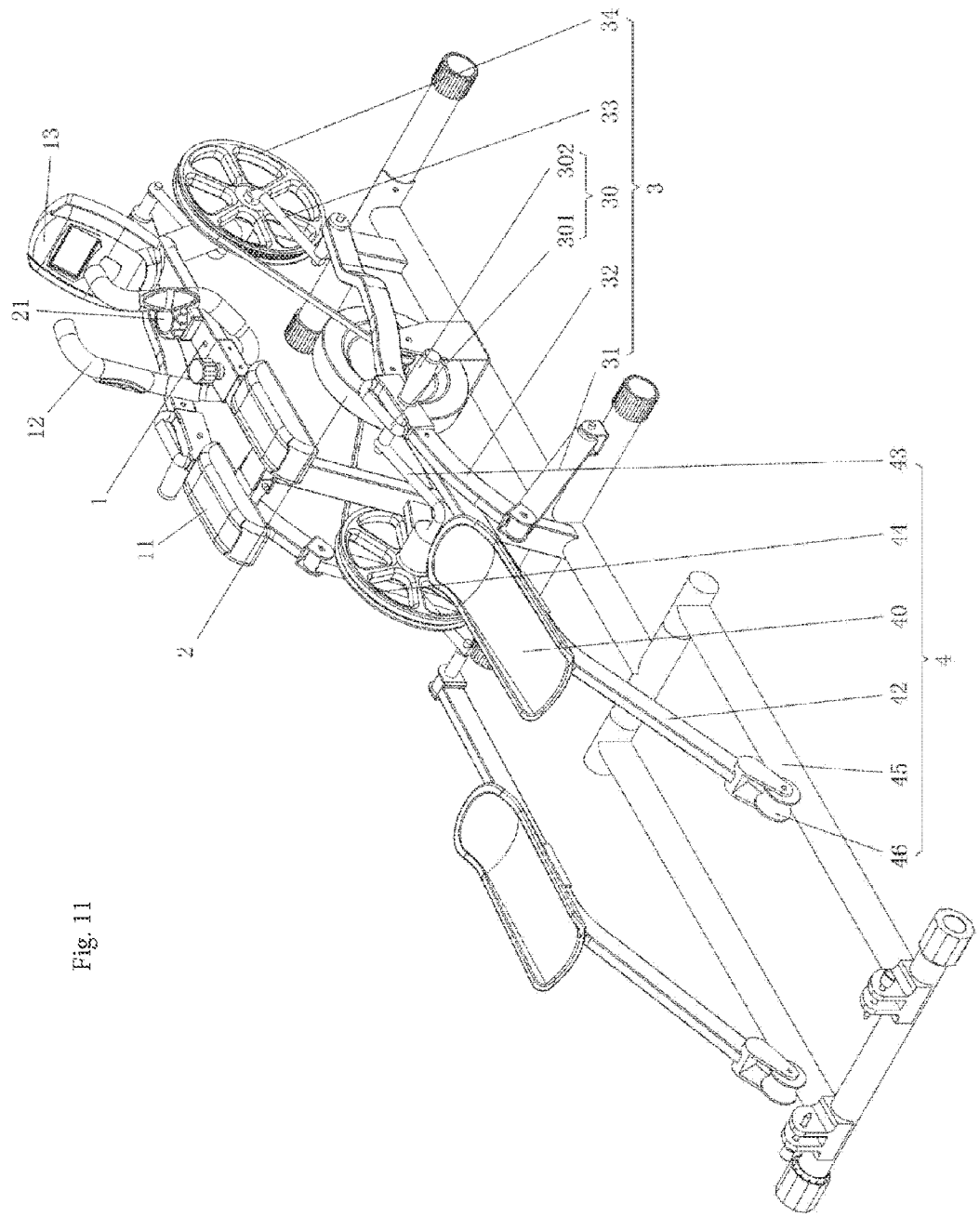
FIG. 11 is a first perspective view showing the three-dimensional structure of Embodiment 4.
Figure 12:
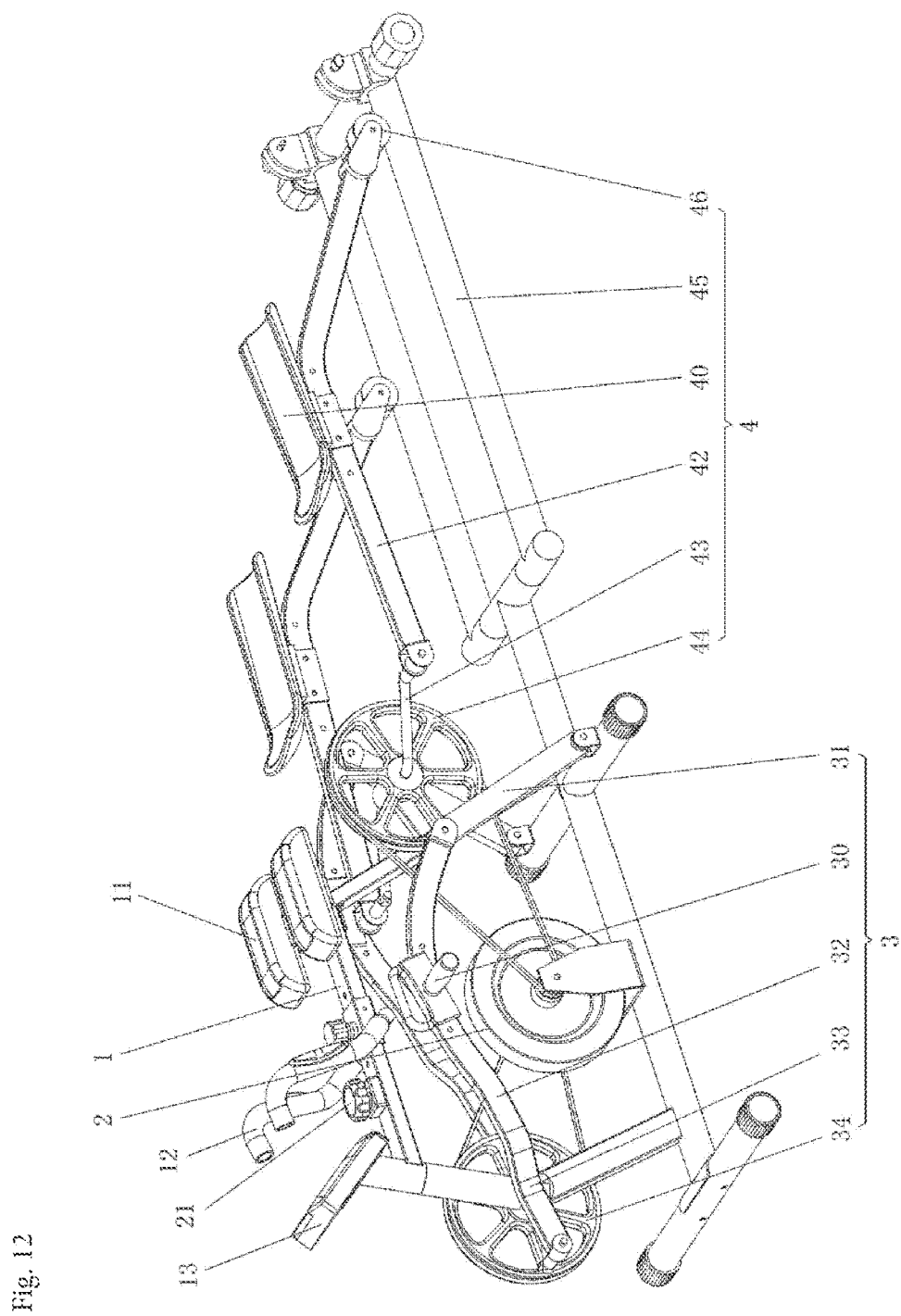
FIG. 12 is a second perspective view showing the three-dimensional structure of Embodiment 4.

Embodiment 4: the forth embodiment of an elliptical prone exerciser is shown in FIG. 11 and FIG. 12. This embodiment is basically the same as Embodiment 3, with the difference in that: with the extended knee pad, the movable knee supporting member 40 can support the whole calf, and therefore, the rear drive mechanism 4 needs not to be provided with pedals 47.

Figure 13:
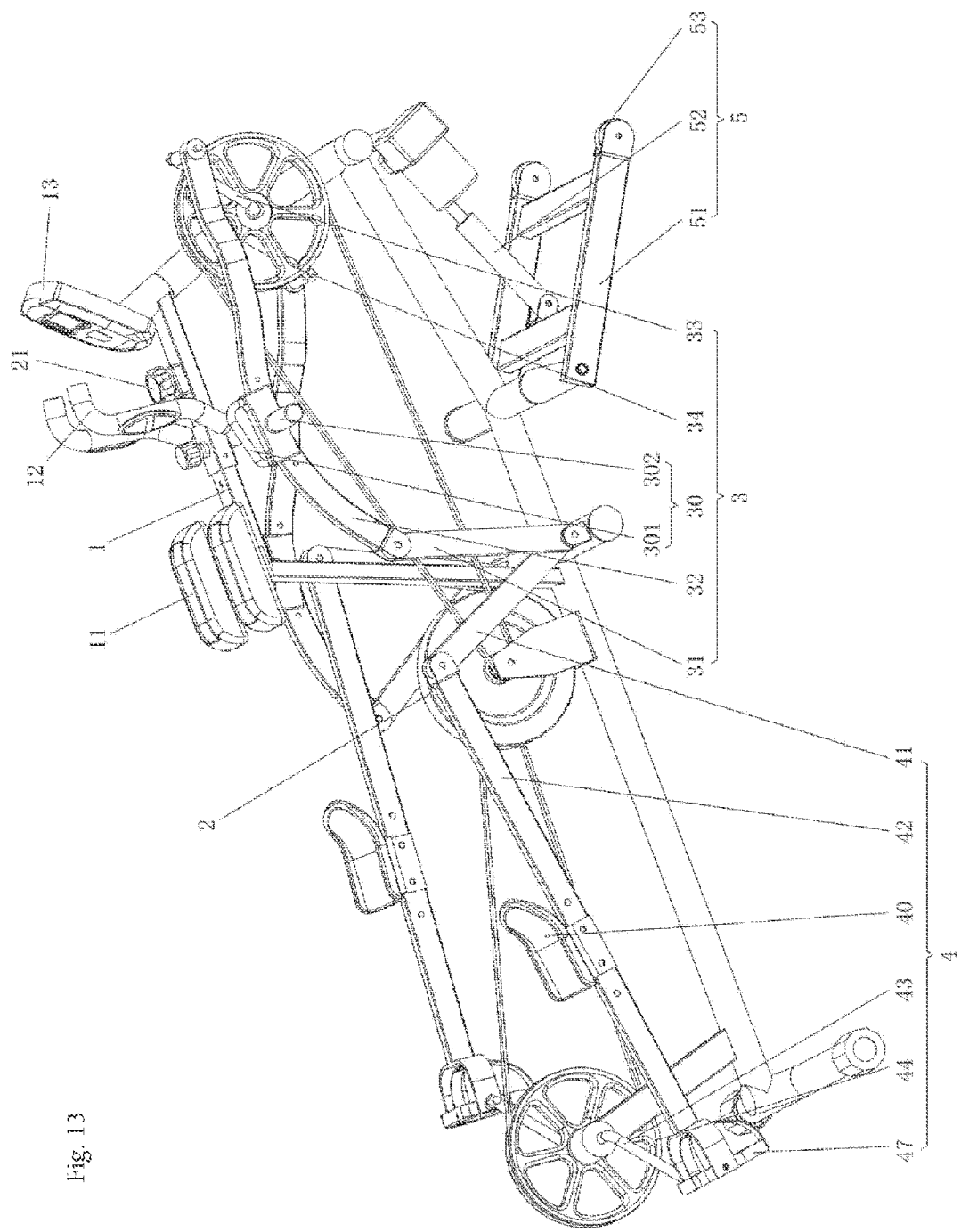
FIG. 13 is a first perspective view showing the three-dimensional structure of Embodiment 5.
Figure 14:
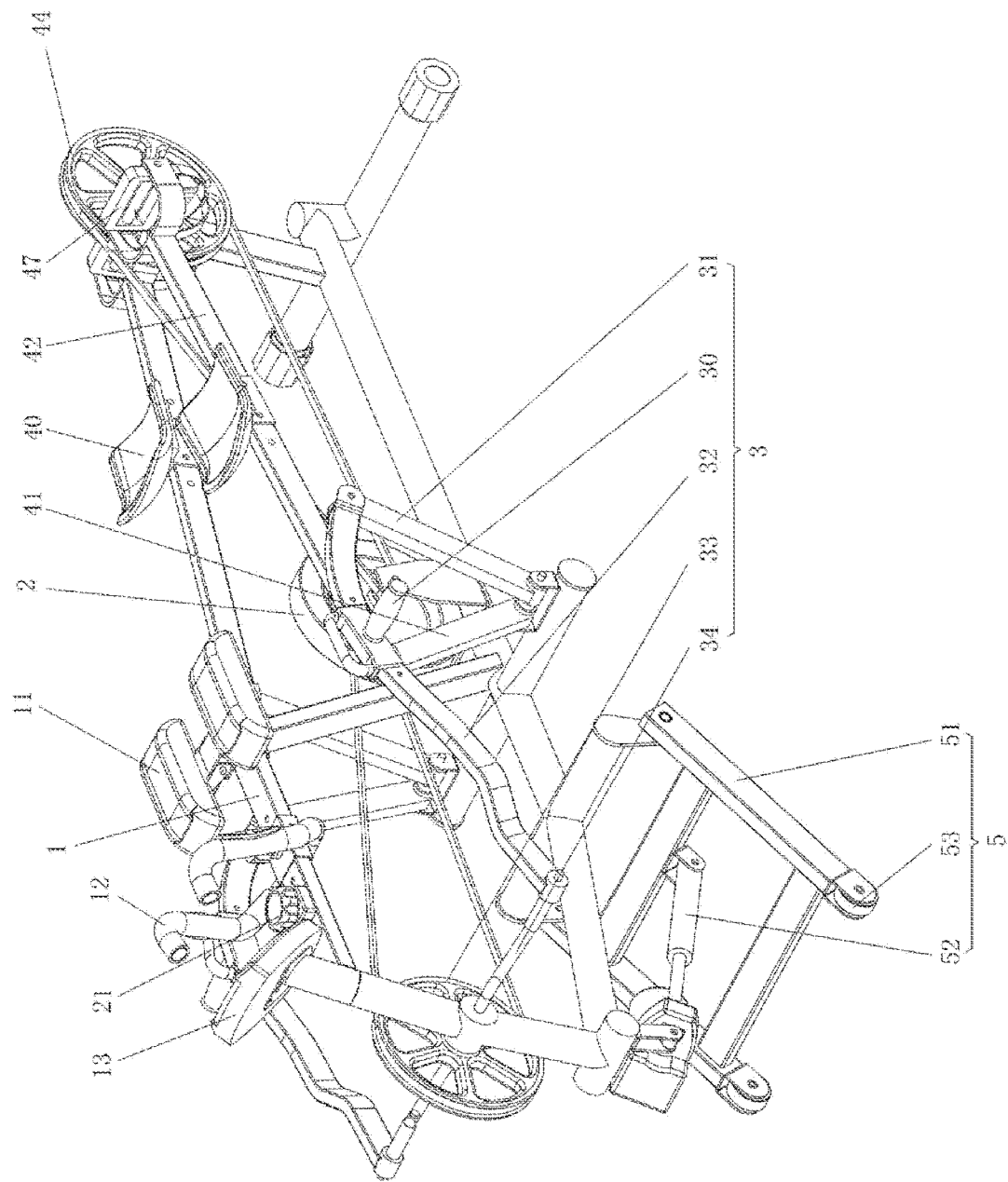
FIG. 14 is a second perspective view showing the three-dimensional structure of Embodiment 5.
Figure 15:
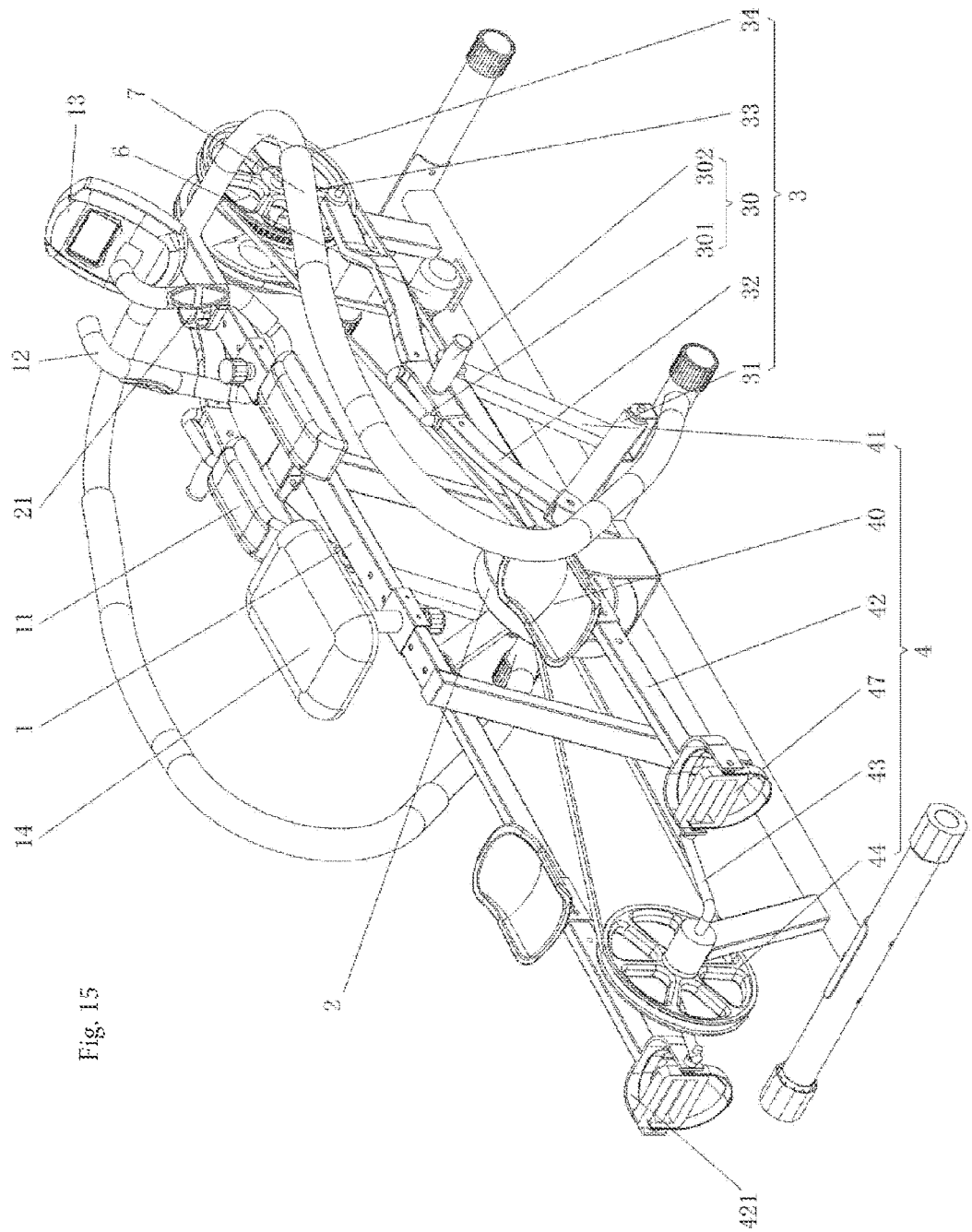
FIG. 15 is a first perspective view showing the three-dimensional structure of Embodiment 6.
Figure 16:
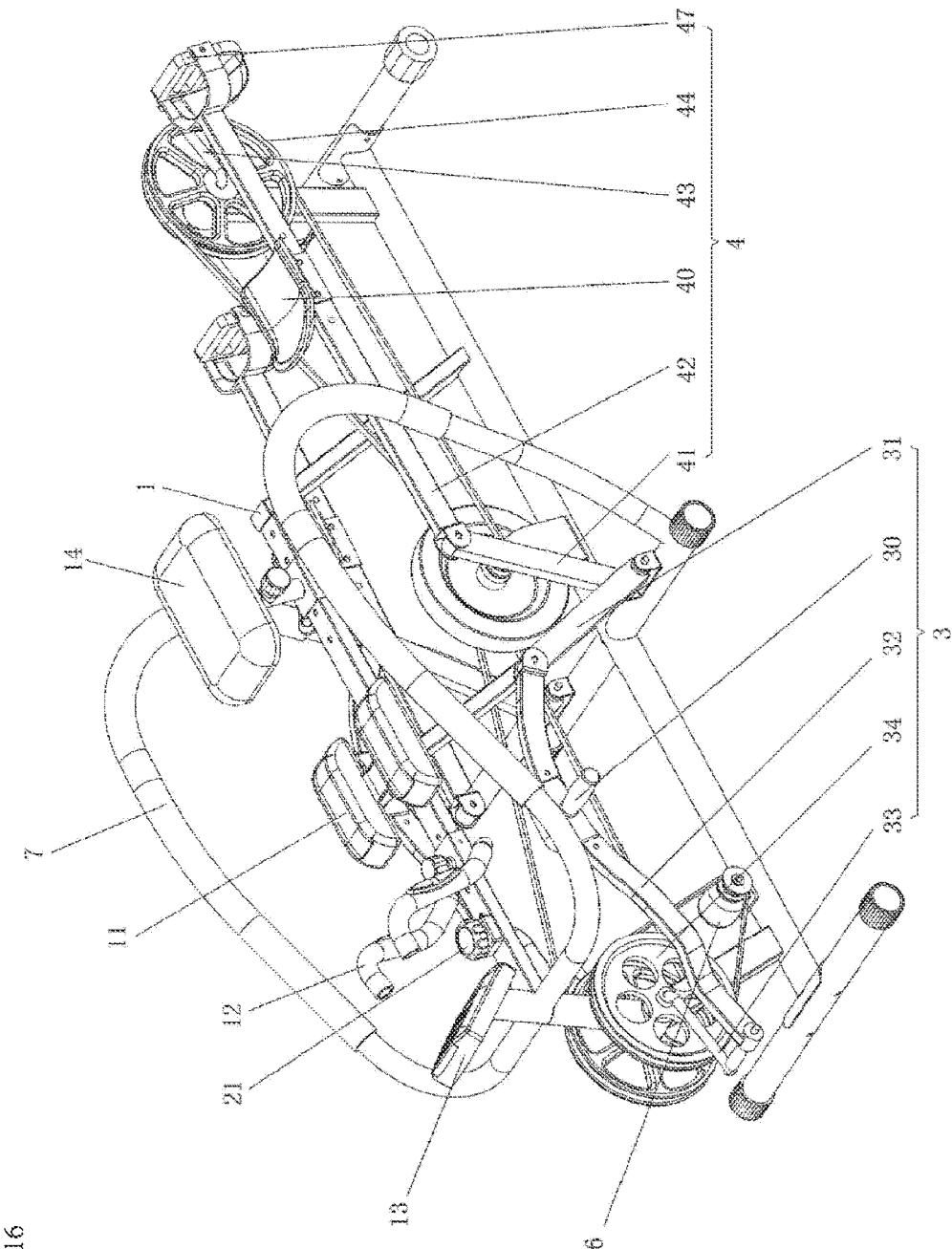
FIG. 16 is a second perspective view showing the three-dimensional structure of Embodiment 6.
Figure 17:
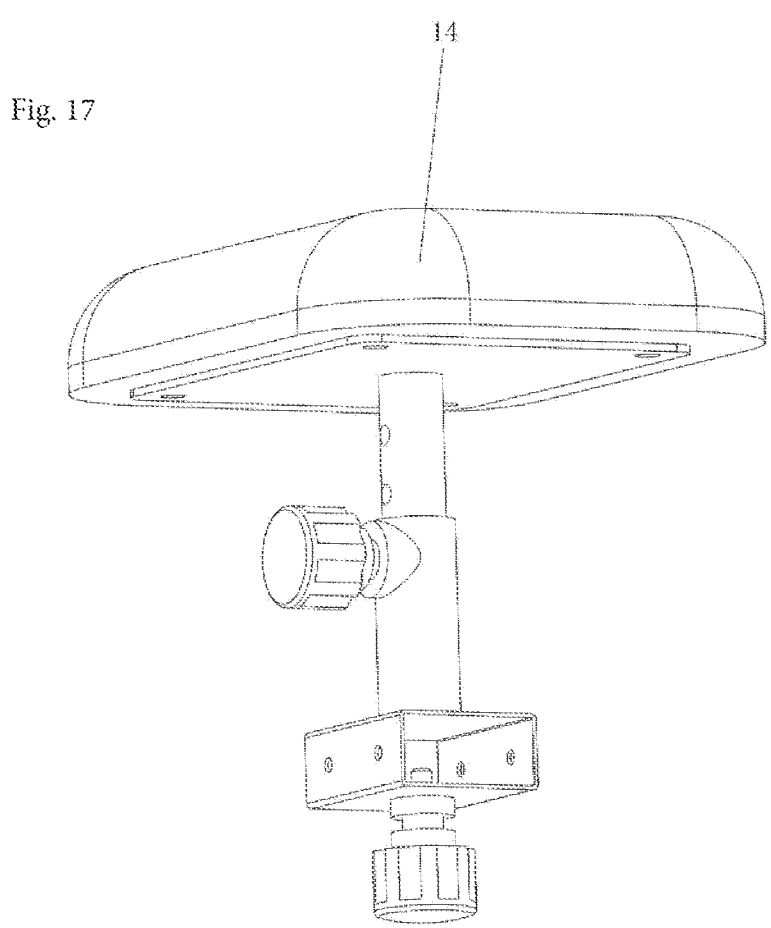
FIG. 17 is a view showing the three-dimensional structure of the chest and abdomen pad of Embodiment 6.
Figure 18:
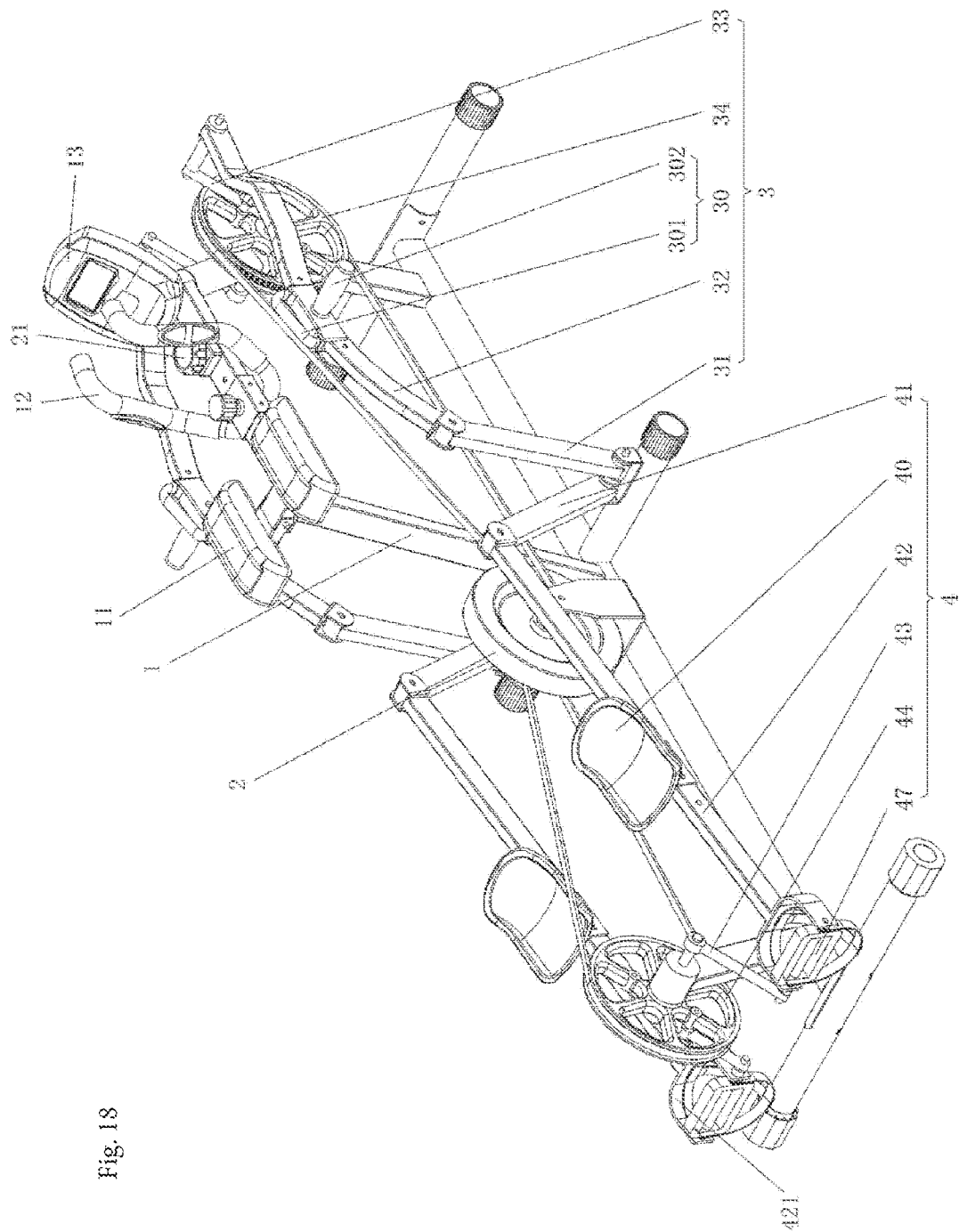
FIG. 18 is a first perspective view showing the three-dimensional structure of Embodiment 7.
Figure 19:
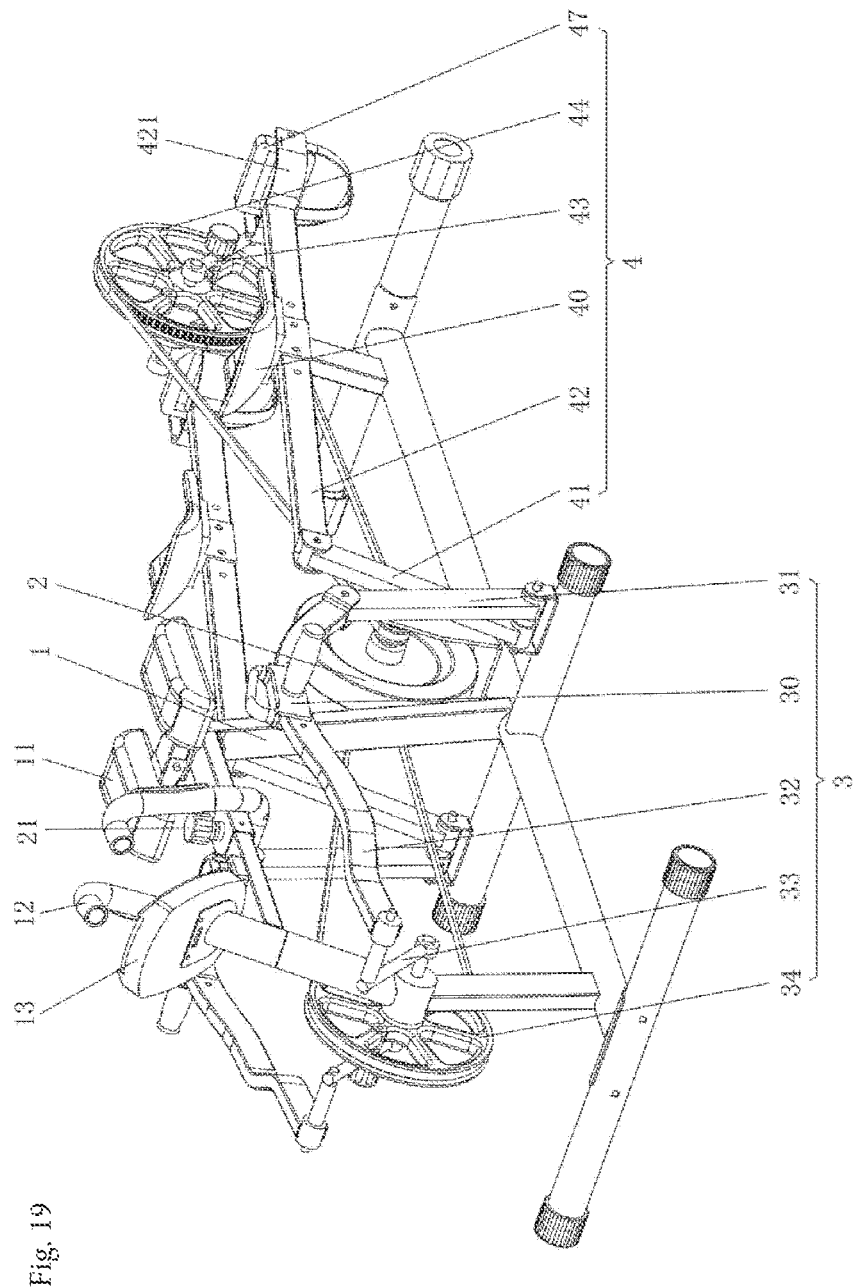
FIG. 19 is a second perspective view showing the three-dimensional structure of Embodiment 7.

Embodiment 5: the fifth embodiment of an elliptical prone exerciser is shown in FIG. 13 and FIG. 14. This embodiment is basically the same as Embodiment 2, with difference in that: an adjusting device 5 used for adjusting the incline angle is arranged on the frame 1, which comprises an adjusting bracket 51 and an extension pushrod 52; one end of the adjusting bracket 51 is articulated with the front part of the frame 1 while the other end is provided with a glide wheel 53; and one end of the extension pushrod 52 is articulated with the adjusting bracket 51 while the other end is articulated with the frame 1. The extension pushrod 52 can be driven by a motor or by hand, and this embodiment chooses motor drive. When the extension pushrod 52 pushes out, the incline angle of the frame 1 increases, and when the extension pushrod 52 draws back, the incline angle of the frame 1 decrease:

Embodiment 6: the sixth embodiment of an elliptical prone exerciser is shown in FIGS. 15 to 17. This embodiment is basically the same as Embodiment 2, with difference in that: the front drive mechanism 3 or the rear drive mechanism 4 is provided with a motor drive device 6 used for providing driving force. In this embodiment, the motor drive device 6 is arranged on the front drive mechanism 3, with the output end thereof connected with the front-drive synchronous transmission pair 34 of the front drive mechanism 3. When the motor drive device 6 is enabled, the user is in passive motion, which is especially suitable for physically weak users or users who need rehabilitation training In this embodiment, the frame 1 is provided with a pair of safe handrails 7 which are separately arranged at two sides of the front-drive mechanism 3. The safe handrails 7 are capable of providing security in exercise.

In this embodiment, a chest and abdomen pad 14 is arranged in the middle of the frame 1. The chest and abdomen pad 14 can be dismantled, or moved forward and backward, or adjustment in height, up to the free choice of users.

Embodiment 7: the seventh embodiment of an elliptical prone exerciser is shown in FIGS. 18 to 21. This embodiment is basically the same as Embodiment 2, with difference in that: both a pair of movable hand support members 30 and a pair of the movable knee support members 40 are arranged symmetrically. Users can do exercises of motions that mimic animal running or dog paddle swimming.

Figure 20:
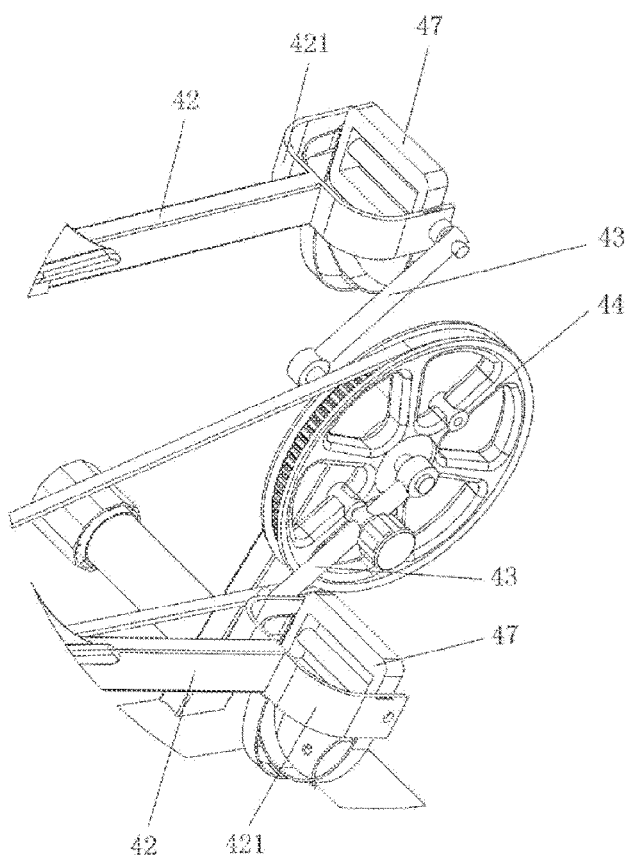
FIG. 20 is a structural view showing the 180° arranged rear-drive cranks of Embodiment 7.
Figure 21:
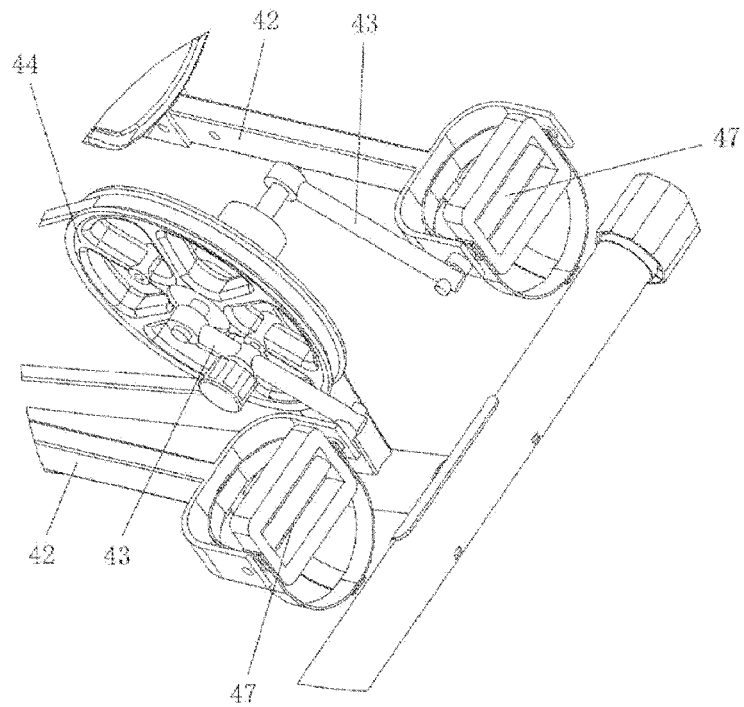
FIG. 21 is a structural view showing the 0° arranged rear-drive cranks of Embodiment 7.
Figure 22:
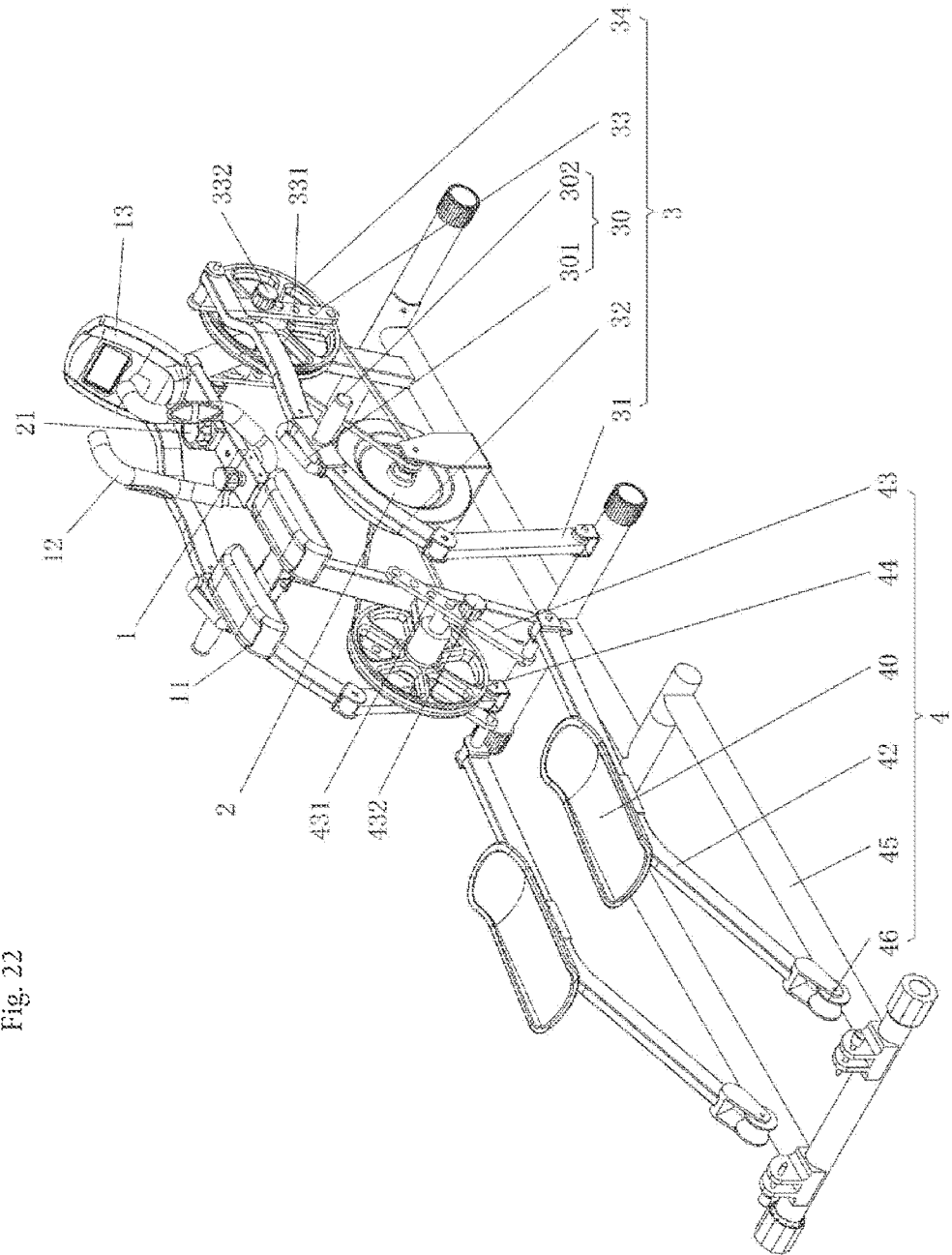
FIG. 22 is a first perspective view showing the three-dimensional structure of Embodiment 8.
Figure 23:
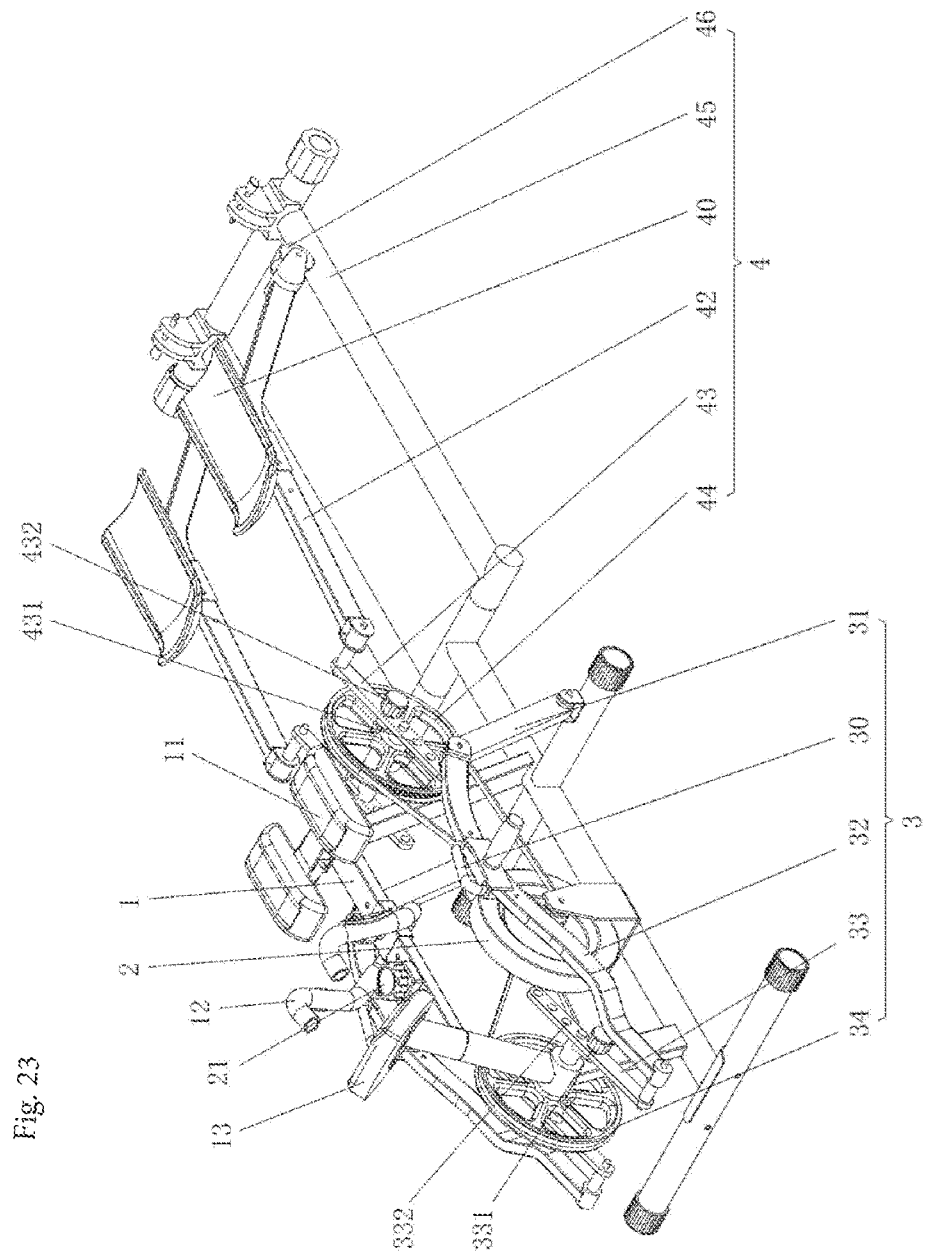
FIG. 23 is a second perspective view showing the three-dimensional structure of Embodiment 8.

As shown in FIG. 20, in a normal use mode, a pair of rear-drive cranks 43 and a pair of front-drive cranks 33 are 180 0 arranged, and users can do crawling exercise. As shown in FIG. 21, a pair of rear-drive cranks 43 and a pair of front-drive cranks 33 are 0° arranged, and users can do running exercise or dog paddle swimming exercise. The shift of the two modes can be realized conveniently by fixing the cranks in corresponding positions with the coordination of a quick plug pin and a belt wheel.

Embodiment 8: the eighth embodiment of an elliptical prone exerciser is shown in FIGS. 22 to 25. This embodiment is basically the same as Embodiment 4, with difference in that: both a pair of movable hand support members 30 and a pair of the movable knee support members 40 are arranged symmetrically. -Users can do exercises of motions that mimic animal running or dog paddle swimming.

In this embodiment, a front-drive synchronous transmission pair 34 comprises a large synchronous belt wheel, a small synchronous belt wheel and a synchronous belt; one side of the large synchronous belt wheel is provided with positioning holes connected with one crank of front-drive crank 33, the other side is provided with a flange arm on which positioning holes connected with another crank of front-drive crank 33 are arranged. A plurality of front-drive crank adjusting holes 331 used for length adjustment are cut on the front-drive cranks 33, and the front-drive cranks 33 are connected with positioning holes on the front-drive synchronous transmission pair 34 by front-drive crank adjusting plug pins 332 which pass through the front-drive crank adjusting holes 331. The coordination between different front-drive crank adjusting holes and positioning holes can change the length of the front-drive cranks 33. A rear-drive synchronous transmission pair 44 comprises a large synchronous belt wheel, a small synchronous belt wheel and a synchronous belt; one side of the large synchronous belt wheel is provided with positioning holes connected with one crank of rear-drive crank 43, the other side is provided with a flange arm on which positioning holes connected with another crank of rear-drive crank 43 are arranged. A plurality of rear-drive crank adjusting holes 431 used for length adjustment are cut on the rear-drive cranks 43, and the rear-drive cranks 43 are connected with positioning holes on the rear-drive synchronous transmission pair 44 by rear-drive crank adjusting plug pins 432 which pass through the rear-drive crank adjusting holes 431. The coordination between different rear-drive crank adjusting holes and positioning holes can change the length of the rear-drive cranks 43. The length of the front-drive cranks 33 can be different with that of the rear-drive cranks 43, but the cranks in the pair of front-drive cranks 33 must be of the same length, so are the cranks in the pair of rear-drive cranks 43.

Figure 24:
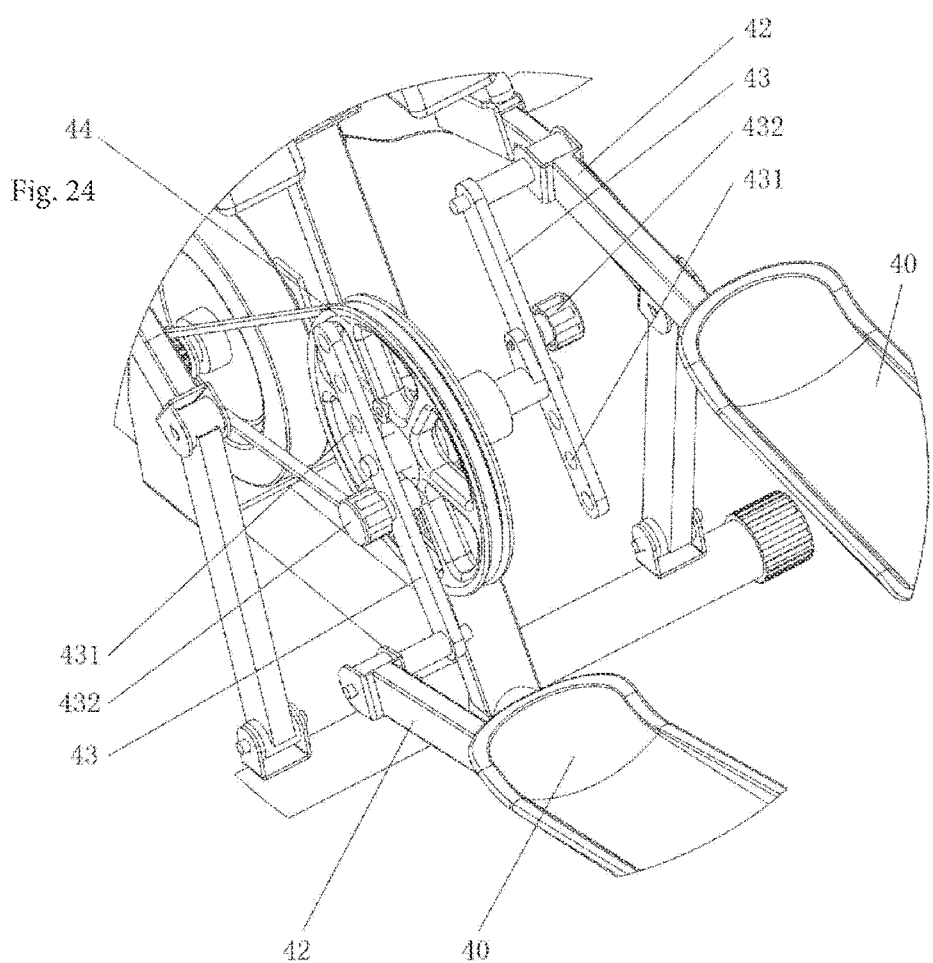
FIG. 24 is a structural view showing the 180° arranged rear-drive cranks of Embodiment 8.
Figure 25:
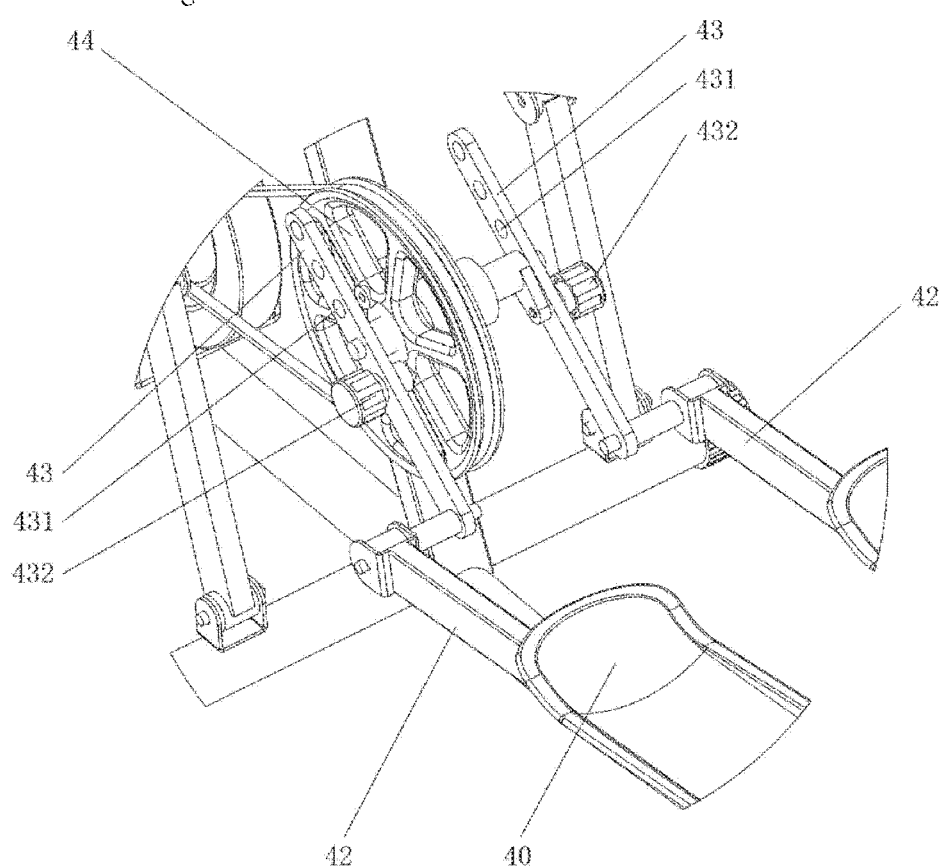
FIG. 25 is a structural view showing the 0° arranged rear-drive cranks of Embodiment 8.

As shown in FIG. 24, in a normal use mode, a pair of rear-drive cranks 43 and a pair of front-drive cranks 33 are 180° arranged, and users can do normal crawling exercise. As shown in FIG. 25, a pair of rear-drive cranks 43 and a pair of front-drive cranks 33 are 0° arranged, and users can do running exercise or dog paddle swimming exercise. The shift of the two modes can be realized conveniently by fixing the cranks in corresponding positions with the coordination of a quick plug pin and a belt wheel.

Though the invention has been disclosed with preferred embodiments above, these specific embodiments disclosed are not intended to limit the invention to the particular forms disclosed. Those skilled in the art may make numerous modifications, variations and equivalents in light of above-described preferred embodiments without departing from the scope and spirit of the invention. Therefore, all such modifications, equivalents and alternatives, without departing from the scope and spirit of the invention, shall fall within the protection scope of the invention.

What is claimed is:

1. An elliptical prone exerciser, comprising a frame (1), a front drive mechanism (3), a rear drive mechanism (4) and a damping wheel (2) arranged on the frame (1), wherein the front drive mechanism (3) and the rear drive mechanism (4) are respectively arranged at a front end and a rear end of the frame (1), an output end of the front drive mechanism (3) and an output end of the rear drive mechanism (4) are respectively connected with the damping wheel (2), the front drive mechanism (3) is provided with a pair of movable hand support members (30), the rear drive mechanism (4) is provided with a pair of movable knee support members (40), wherein the pair of movable hand support members (30) and the pair of movable knee support members (40) move in an elliptical path and are configured to enable hands of a user to be positioned respectively on the pair of movable hand support members (30) and knees of the user to be positioned respectively on the pair of movable knee support members (40), while the user is positioned prone on the elliptical prone exerciser.

2. The elliptical prone exerciser according to claim 1, wherein the front drive mechanism (3) comprises a front-drive synchronous transmission pair (34) as well as a pair of front-drive swinging rods (31), a pair of front-drive connecting rods (32) and a pair of front-drive cranks (33) which are respectively arranged at opposing sides of the front-drive synchronous transmission pair (34); one end of each front-drive swinging rod (31) is articulated with a middle of the frame (1) while another end thereof is articulated with one end of the respective front-drive connecting rod (32); another end of each front-drive connecting rod (32) is articulated with the respective front-drive crank (33); the pair of front-drive cranks (33) is respectively connected with the front-drive synchronous transmission pair (34) and inputted with a rotating torque; an output end of the front-drive synchronous transmission pair (34) is connected with the damping wheel (2); and the pair of movable hand support members (30) is respectively arranged in a middle of each respective front-drive connecting rod (32).

3. The elliptical prone exerciser according to claim 2 wherein the pair of movable hand support members (30) respectively comprises a first gripping part (301) and a second gripping part (302) respectively arranged above and at the side of each respective front-drive connecting rod (32).

4. The elliptical prone exerciser according to claim 1, wherein the rear drive mechanism (4) comprises a rear-drive synchronous transmission pair (44) as well as a pair of rear-drive swinging rods (41), a pair of rear-drive connecting rods (42) and a pair of rear-drive cranks (43) which are respectively arranged at opposing sides of the rear-drive synchronous transmission pair (44); one end of each rear-drive swinging rod (41) is articulated with a middle of the frame (1) while another end thereof is articulated with one end of the respective rear-drive connecting rod (42); another end of each rear-drive connecting rod (42) is articulated with the respective rear-drive crank (43); the pair of rear-drive cranks (43) is respectively connected with the rear-drive synchronous transmission pair (44) and inputted with a rotating torque; an output end of the rear-drive synchronous transmission pair (44) is connected with the damping wheel (2); and the pair of movable knee support members (40) is respectively arranged in a middle of the respective rear-drive connecting rod (42).

5. The elliptical prone exerciser according to claim 4, wherein the pair of movable knee support members (40) is respectively arranged above or hanged at one side of each respective rear-drive connecting rod (42).

6. The elliptical prone exerciser according to claim 4, wherein a pedal (47) is arranged at a joint where each rear-drive connecting rod (42) is articulated with the respective rear-drive crank (43).

7. The elliptical prone exerciser according to claim 6, wherein a U-shaped connector (421) is arranged at the joint where each rear-drive connecting rod (42) is articulated with the respective rear-drive crank (43), and two ends of each U-shaped connector (421) are respectively connected with two ends of a revolving shaft of the respective pedal (47).

8. The elliptical prone exerciser according to claim 7, wherein a plurality of rear-drive crank adjusting holes (431) used for length adjustment are respectively cut on the pair of rear-drive b33cranks (43), and the pair of rear-drive cranks (43) is respectively connected with the rear-drive synchronous transmission pair (44) by respective rear-drive crank adjusting plug pins (432) which pass through the respective rear-drive crank adjusting holes (431).

9. The elliptical prone exerciser according to claim 4, wherein a plurality of rear-drive crank adjusting holes (431) used for length adjustment b32are respectively cut on the pair of rear-drive cranks (43), and the pair of rear-drive cranks (43) is respectively connected with the rear-drive synchronous transmission pair (44) by respective rear-drive crank adjusting plug pins (432) which pass through the respective rear-drive crank adjusting holes (431).

10. The elliptical prone exerciser according to claim 1, wherein the rear drive mechanism (4) comprises a rear-drive synchronous transmission pair (44) as well as a pair of rear-drive guide rails (45), a pair of rear-drive sliding wheels (46), a pair of rear-drive connecting rods (42) and a pair of rear-drive cranks (43) which are respectively arranged at opposing sides of the rear-drive synchronous transmission pair (44); the rear-drive guide rails (45) is connected with the rear end of the frame (1); one end of each rear-drive connecting rod (42) is slidingly-arranged on the respective rear-drive guide rail (45) through the respective rear-drive sliding wheel (46) while another end thereof is articulated with the respective rear-drive crank (43); the pair of rear drive cranks (43) are respectively connected with the rear-drive synchronous transmission pair (44) and inputted with a rotating torque; an output end of the rear-drive synchronous transmission pair (44) is connected with the damping wheel (2); and the pair of movable knee support members (40) is respectively arranged in a middle of the respective rear-drive connecting rod (42).

11. The elliptical prone exerciser according to claim 10, wherein the pedals (47) are respectively arranged on the respective rear-drive connecting rod (42) in a position near the respective rear-drive sliding wheel (46).

12. The elliptical prone exerciser according to claim 10, wherein a front end of the rear-drive guide rail (45) is articulated with the rear end of the frame (1) and a positioning device (48) used for the folding and fixing of each rear-drive guide rail (45) against the frame (1) is arranged on each rear-drive guide rail (45).

13. The elliptical prone exerciser according to claim 10, wherein a plurality of rear-drive crank adjusting holes (431) used for length adjustment are respectively cut on the pair of rear-drive cranks (43), and the pair of rear-drive b34cranks

(43) is respectively connected with the rear-drive synchronous transmission pair (44) by respective rear-drive crank adjusting plug pins (432) which pass through the respective rear-drive crank adjusting holes (431).

14. The elliptical prone exerciser according to claim 1, wherein an adjusting device (5) used for adjusting an incline angle is arranged on the frame (1), the adjusting device (5) comprising an adjusting bracket (51) and an extension pushrod.(52); one end of the adjusting bracket (51) is articulated with a front part of the frame (1) while another end thereof is provided with a glide wheel (53); and one end of the extension pushrod (52) is articulated with the adjusting bracket (51) while another end thereof is articulated with the frame (1).

15. The elliptical prone exerciser according to claim 1, wherein the front drive mechanism (3) or the rear drive mechanism (4) is provided with a motor drive device (6) used for providing driving force.

16. The elliptical prone exerciser according to claim 1, wherein the frame (1) is provided with a pair of safe handrails (7) which are separately arranged at two sides of the front drive mechanism (3).

17. The elliptical prone exerciser according to claim 1, wherein a front part of the frame (1) is provided with an elbow supporting pad (11), a heart-rate monitoring handle (12) and a data display (13); the data display (13) is fixed at the front end of the frame (1); and the heart-rate monitoring handle (12) is arranged between the elbow supporting pad (11) and the data display (13).

18. The elliptical prone exerciser according to claim 1, wherein a chest and abdomen pad (14) is arranged in a middle of the frame (1).

19. The elliptical prone exerciser according to claim 1, wherein the damping wheel (2) is an inertial wheel or a magnetic-control wheel.

20. The elliptical prone exerciser according to claim 1, wherein both the pair of movable hand supports members (30) and the pair of the movable knee support members (40) are arranged symmetrically.

21. The elliptical prone exerciser according to claim 1, wherein a plurality of front-drive crank adjusting holes (331) used for length adjustment are respectively cut on a pair of front-drive cranks (33), and the pair of front-drive cranks (33) is respectively connected with a front-drive synchronous transmission pair (34) by respective front-drive crank adjusting plug pins (332) which pass through the respective front-drive crank adjusting holes (331).

\* \* \* \* \*